United States Patent
Nishimura et al.

(10) Patent No.: US 8,883,977 B2
(45) Date of Patent: Nov. 11, 2014

(54) MUC1 ANTIBODY

(75) Inventors: Shin-Ichiro Nishimura, Sapporo (JP); Shoichi Naito, Toyonaka (JP); Naoki Ohyabu, Toyonaka (JP); Tatsuya Takahashi, Toyonaka (JP); Yoshito Numata, Toyonaka (JP); Keiko Kawamoto, Toyonaka (JP)

(73) Assignees: Shionogi & Co., Ltd., Osaka (JP); National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 13/643,168

(22) PCT Filed: Apr. 28, 2011

(86) PCT No.: PCT/JP2011/002520
§ 371 (c)(1),
(2), (4) Date: Oct. 24, 2012

(87) PCT Pub. No.: WO2011/135869
PCT Pub. Date: Nov. 3, 2011

(65) Prior Publication Data
US 2013/0045543 A1 Feb. 21, 2013

(30) Foreign Application Priority Data
Apr. 28, 2010 (JP) .................................. 2010-104033

(51) Int. Cl.
C07K 16/18 (2006.01)
A61K 39/00 (2006.01)
A61K 39/395 (2006.01)
A61K 49/16 (2006.01)
G01N 33/574 (2006.01)
C07K 16/30 (2006.01)

(52) U.S. Cl.
CPC ...... *G01N 33/57484* (2013.01); *C07K 2317/73* (2013.01); *C07K 16/3092* (2013.01); *A61K 2039/545* (2013.01)
USPC .................................. 530/387.1; 530/388.9

(58) Field of Classification Search
CPC .......... C07K 16/3092; C07K 14/4727; C07K 16/00; C07K 2317/34; C07K 17/732; G01N 33/57484; C12P 21/005; A61K 2039/505; A61K 38/00; A61K 39/00; A61K 39/39533; A61K 51/1645; A61K 2039/009
See application file for complete search history.

(56) References Cited

U.S. PATENT DOCUMENTS

| | | | |
|---|---|---|---|
| 5,506,343 | A | 4/1996 | Kufe |
| 2006/0292643 | A1 | 12/2006 | Goletz et al. |
| 2010/0075344 | A1 | 3/2010 | Vuskovic et al. |
| 2012/0040375 | A1 | 2/2012 | Nishimura et al. |

FOREIGN PATENT DOCUMENTS

| | | |
|---|---|---|
| WO | 99/40881 | 8/1999 |
| WO | 01/12217 | 2/2001 |
| WO | 2008/040362 | 4/2008 |

OTHER PUBLICATIONS

Sorensen et al. Chemoenzymatically synthesized multimeric Tn/STn MUC1 glycopeptides elicit cancer-specific anti-MUC1 antibody responses and overrride tolerance.Glycobiology, 2006, vol. 16, No. 2, pp. 96-107.*
Gura. System for identifying new drugs are often faulty. Science, 1997, vol. 278, pp. 1041-1042.*
Kaiser. First pass at cancer genome reveals complex landscape. Science 2006, vol. 313, pp. 1370.*
Rudikoff et al. Single amino acid substitution altering antigen-binding specificity. PNAS 1982, vol. 79, pp. 1979-1983.*
International Search Report issued Jul. 19, 2011 in International (PCT) Application No. PCT/JP2011/002520.
A. Danielczyk et al., "PankoMab: A Potent New Generation Anti-Tumor MUC1 Antibody", Cancer Immunol Immunother, vol. 55, pp. 1337-1347, 2006.
K. Ryuko et al., "Characterization of a New MUC1 Monoclonal Antibody (VU-2-G7) Directed to the Glycosylated PDTR Sequence of MUC1", Tumor Biology, vol. 21, pp. 197-210, 2000.
N. Ohyabu et al., "As Essential Epitope of Anti-MUC1 Monoclonal Antibody KL-6 Revealed by Focused Glycopeptide Library", J. Am. Chem. Soc., vol. 131, No. 47, pp. 17102-17109, 2009.
M. A. Tarp et al., "Identification of a Novel Cancer-Specific Immunodominant Glycopeptide Epitope in the MUC1 Tandem Repeat", Glycobiology, vol. 17, No. 2, pp. 197-209, 2007.
S. V. Mensdorff-Pouilly et al., "Reactivity of Natural and Induced Human Antibodies to MUC1 Mucin with MUC1 Peptides and N-Acetylgalactosamine (GalNAc) Peptides", Int. J. Cancer, vol. 86, No. 5, pp. 702-712, 2000.

* cited by examiner

*Primary Examiner* — Shafiqul Haq
(74) *Attorney, Agent, or Firm* — Wenderoth, Lind & Ponack L.L.P.

(57) ABSTRACT

An objective of the present invention is to provide a MUC1 antibody having high specificity to cancer cells. The objective has been achieved by the present inventors who found that a cancer-specific sugar chain can be specifically recognized in MUC1 and a cancer cell expressing MUC1 having such a cancer cell specific sugar chain can be recognized. The present invention provides an antibody, an antigen-binding fragment thereof or a MUC1-binding molecule, having, for example, 40-fold specificity or more for a cancer-associated structure of MUC1 as compared to that of a normal tissue-associated structure of MUC1.

12 Claims, 3 Drawing Sheets

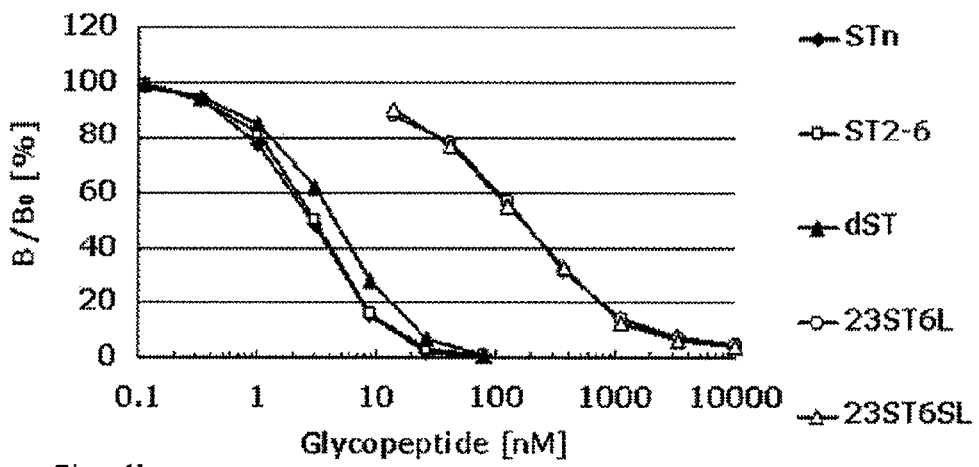
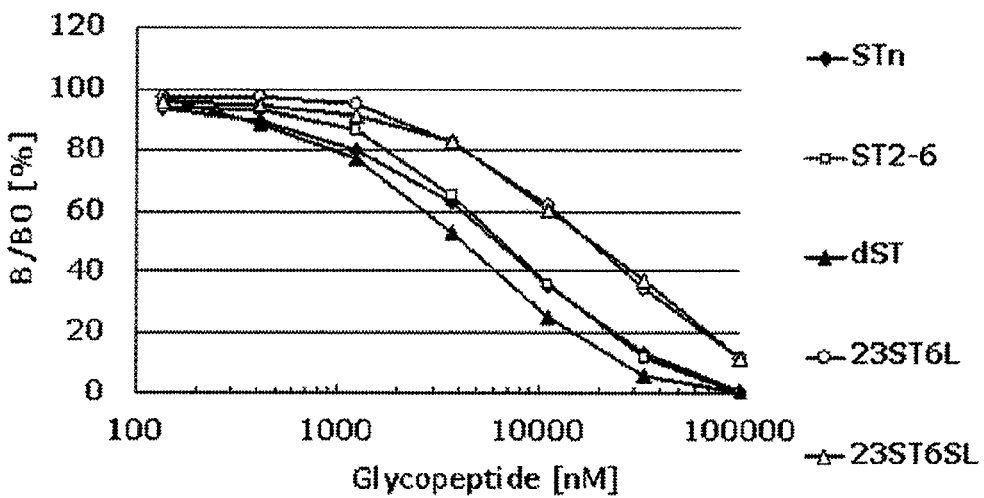
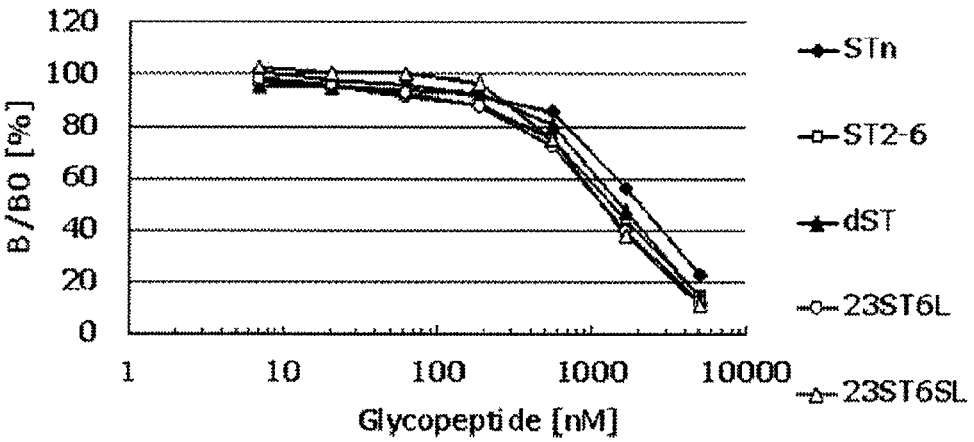

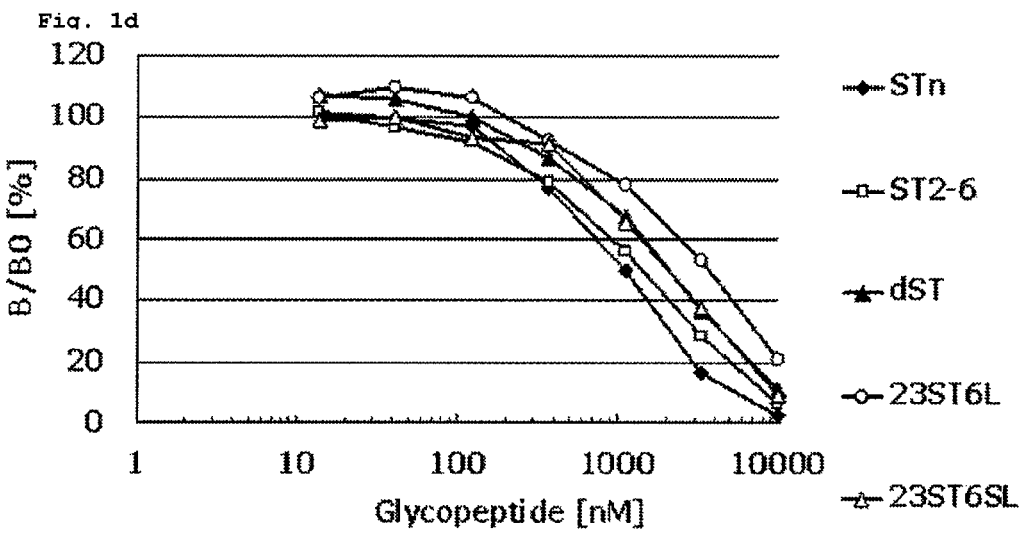
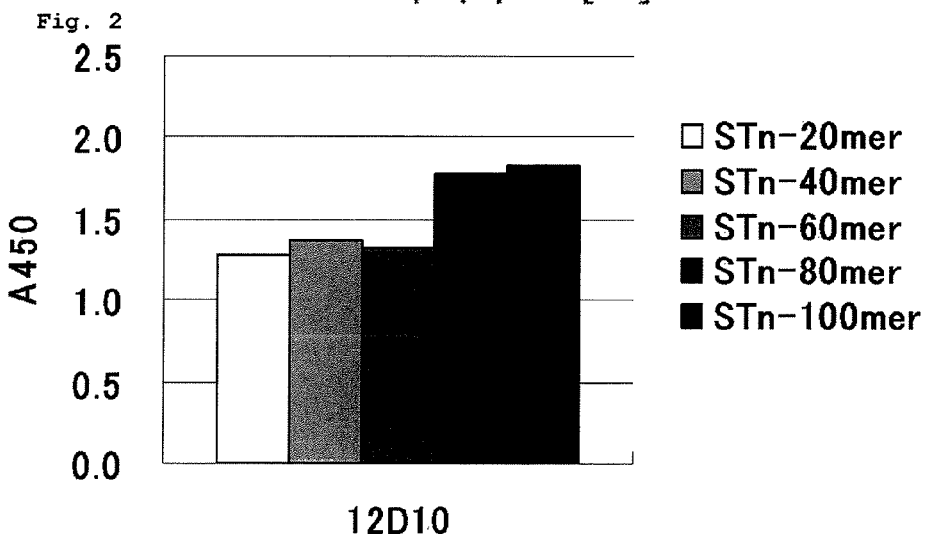
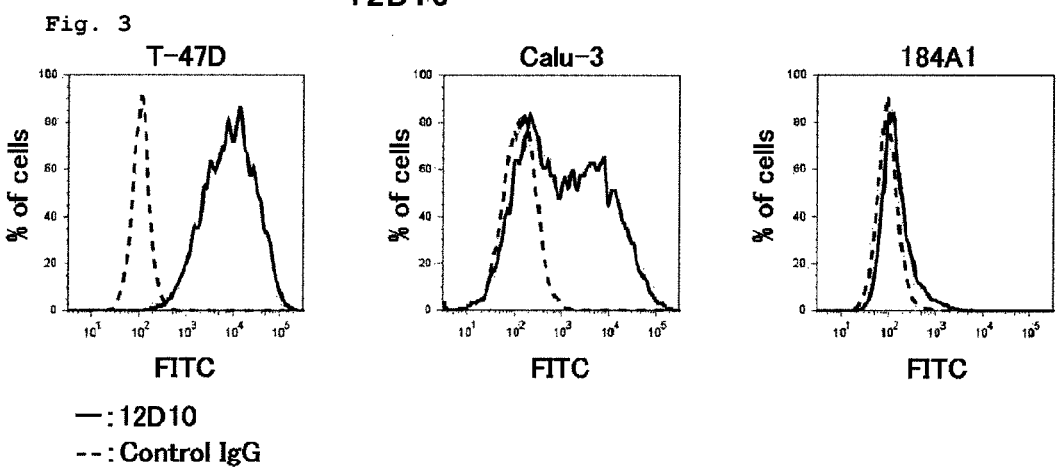

Fig. 4
Heavy chain

VH   1: EVQLVESGGGLVQPGESLKLSCESNEYEFP<u>SHDMS</u>WVRKTPEKRLELVA<u>AINSDGDNTYY</u>   60
                                        CDR1                    CDR2

VH  61: <u>PDTMERRF</u>IISRDNSKKTLYLQMSSLNSADTALYYCARL<u>TLRNWYFDV</u>WGAGTTVTVSS   119
                                              CDR3

Light chain

VH   1: DIVMSQSPSSLPVSVGEKVTMSC<u>KSSQSLLYSTNQQNYLA</u>WYQQKSGQSPKLLVY<u>WASTR</u>   60
                                CDR1'                              CDR2'

VH  61: <u>ES</u>GVPDRFTGSGSGTDFTLTISSLKAEDLAVYYC<u>QQYYRYPPT</u>FGAGTKLELNRA   115
                                          CDR3'

Fig. 5

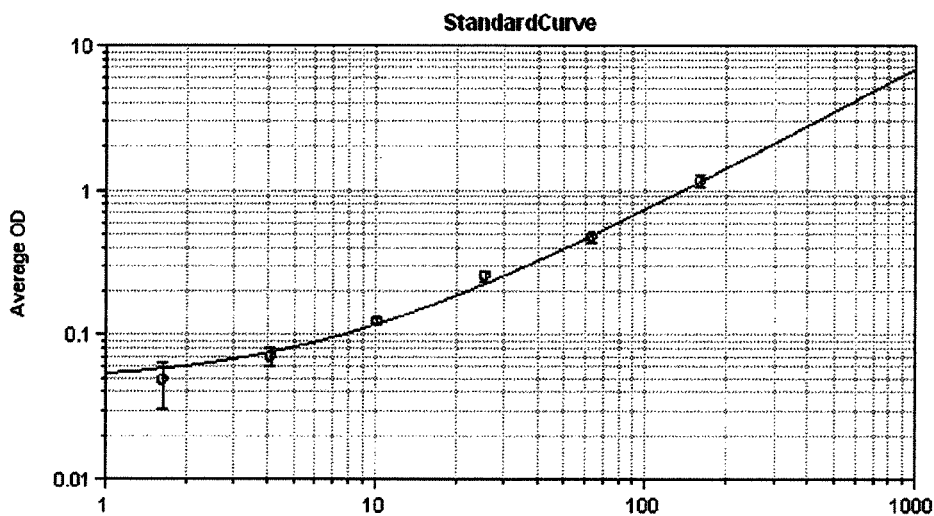

MUC1 ANTIBODY

TECHNICAL FIELD

The present invention relates to a technique in the field of antibodies. More particularly, the present invention relates to an antibody against mucin-1 and a technique for treating cancer using the antibody.

BACKGROUND ART

Mucin-1 (Mucin1, also described as MUC1 hereinafter), which is one kind of mucin, is a tumor-associated antigen; and MUC1 is a high molecular weight glycoprotein which is expressed by many adenocarcinomas. It is known that the extracellular domain, which is essential to the protein, of the membrane glycoprotein is mainly composed of 30 to 90 tandem-type repeats of a core sequence of 20 amino acids (also referred to as "Tn20-mer" hereinafter in the present description; HGVTSAPDTRPAPGSTAPPA (SEQ ID No.: 1)) rich in serine, threonine and proline. The repetition number of the "Tn20-mer" expressed is different depending on the individual pieces. The repetition number is genetically determined, resulting in size polymorphisms.

Tumor MUC1 generally has low glycosylation, and comprises one or more glycosylation sites frequently with abnormal sugar chain extension. This abnormal glycosylation generates the result of exposure of a normal cryptic peptide epitope and the creation of a novel carbohydrate epitope. Due to their high molecular weight ($2\times10^5$ to $5\times10^7$ daltons) and extensive glycosylation, a cellular membrane mucin is present as a soft rod, and protrudes from a cellular surface at a relatively large distance. Therefore, the mucin forms an important component of the polysaccharide coat, and is probably the first point of cellular contact between an antibody and an immune system cell.

A large number of monoclonal antibodies (MAb) to purified MUC1 and to synthetic peptides and glycopeptides derived from MUC1 have been previously produced (Patent Documents 1 to 5 and Non-Patent Documents 1 and 2). Most of the minimum sequence recognition of these antibodies are thought to be present within APDTRPAP (SEQ ID NO: 10). The sequence SAPDTRP (SEQ ID NO: 11) in a MUC1 tandem-type repetition is an immunodominant B cell epitope, and the sequence PDTRP (SEQ ID NO: 12) is positioned at a T-cell epitope of tandem-type repetition. Since the threonine included in these sequences is heavily O-glycosylated, the threonine is thought to affect the selectivity of antibodies binding to MUC1 and the affinity thereof. However, while the monoclonal antibodies described above were able to recognize the difference in the peptides, which are epitopes, by the presence or absence of the glycosylation, none of the monoclonal antibodies were able to recognize the difference in the sugar chain structures. Thus, it was not possible to say that the selectivity to cancer cells was sufficient.

PRIOR ART DOCUMENTS

Patent Documents

Patent Document 1: Japanese Patent No. 3698370 specification
Patent Document 2: Japanese National Phase PCT Laid-Open Publication No. 2002-502621
Patent Document 3: Japanese National Phase PCT Laid-Open Publication No. 2003-519096
Patent Document 4: United States Patent Application Publication No. 2006/0292643
Patent Document 5: Japanese National Phase PCT Laid-open Publication No. 2010-505775

Non-Patent Documents

Non-Patent Document 1: Cancer Immunol Immunother 55: 1337-1347 (2006)
Non-Patent Document 2: Tumor Biology Vol. 21, No. 4, 197-210 (2000)

SUMMARY OF THE INVENTION

Problem to be Solved by the Invention

An object of the present invention is to provide an antibody having specificity to a MUC1 cell having a sugar chain structure which is highly expressed in a cancer cell.

Means for Solving the Problems

The objective was achieved through discovery by the present inventors that an antibody obtained from immunizing an animal using an epitope in accordance with an amino acid sequence of a peptide (HGVTSAPDTRPAPGSTAPPA (SEQ ID NO.: 1)), to which an STn-type sugar chain (Compound No.: 4) was added, as an antigen, has specificity for a cancer-specific sugar chain consisting of a plurality of types, and further, has significantly higher specificity for a cancer cell that expresses MUC1 than conventional antibodies.

In another aspect, the present invention provides an antibody, an antigen-binding fragment thereof or a MUC1-binding molecule, having 40-fold specificity or more for a cancer-associated structure of MUC1 as compared to that of a normal tissue-associated structure of MUC1.

More specifically, the present invention provides an antibody, an antigen-binding fragment thereof or a MUC1-binding molecule, in which a cross reactivity ratio of a normal tissue-associated structure of MUC1 to a cancer-associated structure of MUC1 is 40-fold or more, the normal tissue-associated structure being selected from the group consisting of Neu5Acα2→3Galβ1→3[GlcNAcβ1→6]GalNAcα-R, Neu5Acα2→3Galβ1→3[Galβ1→4GlcNAcβ1→6]GalNAcα-R, and Neu5Acα2→3Galβ1→3[Neu5Acα2→3Galβ1→4GlcNAcβ1→6]GalNAcα-R, the cancer-associated structure being selected from the group consisting of Neu5Acα2→6GalNAcα-R (which corresponds to STn (Compound 4) in the present specification), Galβ1→3[Neu5Acα2→6]GalNAcα-R (which corresponds to ST2-6 (Compound 10) in the present specification), and Neu5Acα2→3Galβ1→3[Neu5Acα2→6]GalNAcα-R (which corresponds to dST (Compound 11) in the present specification), where the Neu5Ac is N-acetylneuraminic acid, the Gal is galactose, the GlcNAc is N-acetylglucosamine, the GalNAc is N-acetylgalactosamine, and the R is a non-sugar part.

In another embodiment, the specificity to the cancer-associated structure of the antibody, the antigen-binding fragment thereof or the MUC1-binding molecule of the present invention can be expressed by cross reactivity to STn (Compound 4). The cross reactivity is obtained by the following calculation equation: ($IC_{50}$ for STn (Compound 4)/$IC_{50}$ for sugar chain structure to be compared)$\times100(\%)$. In one embodiment, the antibody of the present invention is indicated to have about 2% or less cross reactivity and have 50-fold specificity or more to any of the normal tissue-associated structures, with regard to the cancer-associated structure, Neu5Acα2→6GalNAcα-R (100%).

In still another aspect, the present invention provides an anti-MUC1 antibody, an antigen-binding fragment thereof or a MUC1-binding molecule, having at least 20-fold specificity or more to a cancer cell compared to the specificity to a normal cell.

In one embodiment, the present invention provides an antibody, an antigen-binding fragment thereof or a MUC1-binding molecule, having about 70-fold specificity to a breast cancer cell compared to the specificity to a mammary gland epithelial cell.

In one embodiment, the present invention provides an antibody, an antigen-binding fragment thereof or a MUC1-binding molecule, where the cross reactivity ratio of the normal tissue-associated structure to the cancer-associated structure of MUC1, Neu5Acα2→6GalNAcα-R, is 50-fold or more.

In one embodiment, the present invention provides an antibody, an antigen-binding fragment thereof or a MUC1-binding molecule, where in an assessment of binding to a cell with FACS, the antibody, the antigen-binding fragment thereof or the MUC1-binding molecule has 100-fold specificity or more to a T-47D cell as compared to specificity to a 184A1 cell when the specificity is assessed with fluorescence signal shift.

In still another aspect, the present invention provides an antibody, an antigen-binding fragment thereof or a MUC1-binding molecule, where tandem repeat dependency of Tn20-mer (or an amino acid represented by SEQ ID NO: 1) is low. Here, for the dependency being low, one of the characteristics is that the ratio (A100/A20) between absorbance at 450 nm in the case of using Tn20-mer biotin (A20) and absorbance at 450 nm in the case of using Tn100-mer biotin (A100) is 2 or less, and preferably 1.5 or less.

Further, in a specific embodiment, the present invention provides an anti-MUC1 antibody, an antigen-binding fragment thereof or a MUC1-binding molecule, comprising at least one antigen-binding site including an immunoglobulin heavy chain variable region (VH) domain and an immunoglobulin light chain variable region (VL) domain, the heavy chain variable region domain containing hypervariable regions, CDR1, CDR2 and CDR3, in a sequence thereof, wherein the CDR1 consists of SHDMS (SEQ ID NO: 4) or a variant thereof, the CDR2 consists of AINSDGDNTYYPDTMER (SEQ ID NO: 5) or a variant thereof, and the CDR3 consists of LTLRNWYFDV (SEQ ID NO: 6) or a variant thereof, the light chain variable region domain containing hypervariable regions, CDR1', CDR2' and CDR3', in a sequence thereof, where the CDR1' consists of KSSQSLLYSTNQQNYLA (SEQ ID NO: 7) or a variant thereof, the CDR2' consists of WASTRES (SEQ ID NO: 8) or a variant thereof, and the CDR3' consists of QQYYRYPPT (SEQ ID NO: 9) or a variant thereof.

More specifically, the present invention relates to an antibody comprising a total length sequence of an antibody 12D10, or SEQ ID NOs: 2 and 3, and an antigen-binding fragment thereof.

In still another aspect, the present invention relates to a medicament comprising the antibody, the antigen-binding fragment thereof or the MUC1-binding molecule of the present invention.

In still another aspect, the medicament of the present invention is an anticancer agent.

In still another aspect, the present invention provides a nucleic acid molecule (e.g. DNA and the like) encoding the antibody, the antigen-binding fragment thereof or the MUC1-binding molecule of the present invention.

In still another aspect, the present invention relates to a diagnosis agent comprising the antibody, the antigen-binding fragment thereof or the MUC1-binding molecule of the present invention.

In still another aspect, the present invention relates to a method for diagnosing cancer using the antibody, the antigen-binding fragment thereof or the MUC1-binding molecule of the present invention.

In still another aspect, the present invention relates to a diagnosis kit comprising the antibody, the antigen-binding fragment thereof or the MUC1-binding molecule of the present invention.

In still another aspect, the present invention relates to an antibody, an antigen-binding fragment thereof or a MUC1-binding molecule of the present invention, which is labeled.

In still another aspect, the present invention relates to an immunoassay using the antibody, the antigen-binding fragment thereof or the MUC1-binding molecule of the present invention.

In still another aspect, the present invention relates to a method for detecting MUC1 or an associated molecule thereof, using the antibody, the antigen-binding fragment thereof or the MUC1-binding molecule of the present invention.

In still another aspect, the present invention relates to a method for screening a biological sample from a cancer patient, comprising the steps of: measuring the amount of a cancer-associated structure of MUC1 in a biological sample using the antibody, the antigen-binding fragment thereof or the MUC1-binding molecule of the present invention; and determining the biological sample as a biological sample from a cancer patient when the amount of the cancer-associated structure of MUC1 in the biological sample is recognized to be more than the amount of a cancer-associated structure of MUC1 in a biological sample from a healthy individual.

The antibody of the present invention has low tandem repeat dependency, and this is useful for the following reasons: many kinds of sugar chains are attached to MUC1, it is expected that antibodies having lower tandem repeat dependency can bind to MUC1 better independent of the number of repeated structures thereof, and the detectability of MUC1 is excellent.

That is, it can be explained that although an antibody having high tandem repeat dependency can strongly bind to only a part where an epitope structure (○) is repeated (affinity for ○-○-○-○-○ is high, but affinity for □-Δ-○-■-▲ is low (wherein ▲, Δ, ■ and □ are different from each other, and each indicates another epitope structure different from ○)), an antibody having low tandem repeat dependency can strongly bind thereto even in the case where the number of epitope structures (○) is one (affinity for ○-○-○-○-○ is high, and affinity for □-Δ-○-■-▲ is also high).

In all these aspects, it is understood that each embodiment described as used herein can be applied to other aspects, as far as it is applicable.

Effect of the Invention

An antibody which specifically binds to a cancer cell without considerably binding to normal cells was provided. This antibody further has the ability to kill cancer cells, and is expected as an anti-cancer agent having few side effects.

BRIEF DESCRIPTION OF THE DRAWINGS

FIG. 1a shows a curve of substitution with various MUC1 glycopeptides for binding of MUC1 antibody (12D10) and sugar chain structure highly expressed in a cancer cell (STn (DT*R)-20 (Compound No. 4 of Table 1)). The ordinate axis indicates a ratio of absorbance at 450 nm when various MUC1 glycopeptides were added, letting absorbance at 450 nm when any MUC1 glycopeptides were not added, to be 100%, and the abscissa axis indicates concentrations of various MUC1 glycopeptides. In any figures, a black diamond indicates STn, a white quadrilateral indicates ST2-6, a black triangle indicates dST, a white circle indicates 23ST6L, and a white triangle indicates 2,3ST6SL.

FIG. 1b shows a curve of substitution with various MUC1 glycopeptides for binding of MUC1 antibody (PankoMab) and sugar chain structure highly expressed in a cancer cell (STn(DT*R)-20 (Compound No. 4 of Table 1)). The ordinate axis indicates a ratio of absorbance at 450 nm when various MUC1 glycopeptides were added, letting absorbance at 450 nm when any MUC1 glycopeptides were not added, to be 100%, and the abscissa axis indicates concentrations of various MUC1 glycopeptides. In any figures, a black diamond indicates STn, a white quadrilateral indicates ST2-6, a black triangle indicates dST, a white circle indicates 23ST6L, and a white triangle indicates 2,3ST6SL.

FIG. 1c shows a curve of substitution with various MUC1 glycopeptides for binding of MUC1 antibody (VU-2G7) and sugar chain structure highly expressed in a cancer cell (STn (DT*R)-20 (Compound No. 4 of Table 1)). The ordinate axis indicates a ratio of absorbance at 450 nm when various MUC1 glycopeptides were added, letting absorbance at 450 nm when various MUC1 glycopeptides were not added, to be 100%, and the abscissa axis indicates concentrations of any MUC1 glycopeptides. In any figures, a black diamond indicates STn, a white quadrilateral indicates ST2-6, a black triangle indicates dST, a white circle indicates 23ST6L, and a white triangle indicates 2,3ST6SL.

FIG. 1d shows a curve of substitution with various MUC1 glycopeptides for binding of MUC1 antibody (SM3) and sugar chain structure highly expressed in a cancer cell (STn (DT*R)-20 (Compound No. 4 of Table 1)). The ordinate axis indicates a ratio of absorbance at 450 nm when various MUC1 glycopeptides were added, letting absorbance at 450 nm when various MUC1 glycopeptides were not added, to be 100%, and the abscissa axis indicates concentrations of various MUC1 glycopeptides. In any figures, a black diamond indicates STn, a white quadrilateral indicates ST2-6, a black triangle indicates dST, a white circle indicates 23ST6L, and a white triangle indicates 2,3ST6SL.

FIG. 2 shows MUC1 tandem repeat dependency of an antibody 12D10. The ordinate axis indicates absorbance at 450 nm, and the abscissa axis indicates a type of the MUC1 glycopeptide. From the left (bar with a white blank inside), the bars indicate a 20-mer (STn-20-mer), a 40-mer (STn-40-mer), a 60-mer (STn-60-mer), a 80-mer (STn-80-mer), and a 100-mer (STn-100-mer) respectively (right end, black bar).

FIG. 3 shows an experimental result of examination with FACS of whether a MUC1 protein expressed on a cancer cell membrane surface binds to a 12D10 antibody or not. The graphs show the result of analysis by FACS Aria. The left part indicates the result on a breast cancer cell T-47D, the center part indicates a human lung cancer cultured cell, Calu-3 cell, and the right part indicates the result on a mammary gland epithelial cell 184A which as a control. A dotted line indicates a control IgG, and a solid line indicates the 12D10 antibody. From this result, it was demonstrated that the 12D10 antibody strongly reacts with a breast cancer cell and a lung cancer cell, but hardly reacts with a mammary gland epithelial cell.

FIG. 4 shows an amino acid sequence of variable regions of the antibody 12D10 (SEQ ID NOs.: 2 and 3). The upper two rows indicate a heavy chain (SEQ ID NO.: 2), and the lower two rows indicate a light chain (SEQ ID NO.: 3). Underlines indicate respective CDR sites.

FIG. 5 shows a standard curve for quantification of MUC1 by a sandwich immunoassay using the antibody 12D10.

MODE FOR CARRYING OUT THE INVENTION

With respect to the present invention, various embodiments will be described below. It should be understood that, throughout the present specification, singular expressions (e.g. "a", "an", "the" etc. in the case of English, corresponding articles, adjectives etc. in other languages) also include concepts of its plural, unless otherwise is indicated. In addition, it should be understood that the terms used herein are used in a sense normally used in the art, unless otherwise is indicated. Therefore, all specialized terminology and scientific and technical terminology used herein have the same meanings as those generally understood by a person skilled in the field to which the present invention belongs, unless defined differently. When there are some inconsistencies, the present specification (including definitions) prevails.

DEFINITION OF TERMINOLOGY

As used herein, "protein", "polypeptide", "oligopeptide" and "peptide" refer to a polymer of an amino acid of any length. This polymer may be linear, branched, or cyclic. The amino acid may be naturally-occurring, non-naturally-occurring, or may be an altered amino acid. This term can also include an assembly of a plurality of polypeptide chains into a complex. This term also includes natural or artificially altered amino acid polymers. Such alteration includes disulfide bond formation, glycosylation, lipidation, acetylation, phosphorylation or any other manipulation or alteration (e.g. conversion into a bound body with a labeling component). This definition also includes, for example, polypeptides including one or two or more analogs of amino acids (e.g. including non-naturally-occurring amino acids), peptide-like compounds (e.g. peptoids) and other alterations known in the art.

As used herein, an "amino acid" may be naturally-occurring or non-naturally-occurring, as far as the object of the present invention is satisfied.

As used herein, "nucleic acid" can also be used interchangeably with a gene, cDNA, mRNA, an oligonucleotide, and a polynucleotide. A particular nucleic acid sequence also includes "splice variants". Similarly, a particular protein encoded by a nucleic acid implicitly includes any protein encoded by a splice variant of the nucleic acid. As suggested by its name, a "splice variant" is a product of alternative splicing of a gene. After transcription, a first nucleic acid transcript can be spliced so that a different (another) nucleic acid splice product encodes a different polypeptide. The mechanism of producing the splice variant includes alternative splicing of an exon as well as other means. A different polypeptide derived from the same nucleic acid by transcription read through is also included in this definition. Any product of a splicing reaction (including a recombinant splice product) is also included in this definition. An allele variant also falls into this range.

As used herein, "polynucleotide", "oligonucleotide" and "nucleic acid" are used in the same sense, and refer to a polymer having a nucleotide of any length. This term also includes "oligonucleotide derivative" or "polynucleotide derivative". "Oligonucleotide derivative" or "polynucleotide derivative" includes a derivative of a nucleotide, or refers to an oligonucleotide or a polynucleotide in which binding between nucleotides is different from normal binding; these are interchangeably used. Examples of such oligonucleotide specifically include 2'-O-methyl-ribonucleotide, an oligonucleotide derivative in which a phosphate diester bond in an oligonucleotide was converted into a phosphorothioate bond, an oligonucleotide derivative in which a phosphate diester bond in an oligonucleotide was converted into an N3'-P5' phosphoroamidate bond, an oligonucleotide derivative in which ribose and a phosphate diester bond in an oligonucleotide were converted into a peptide nucleic acid bond, an oligonucleotide derivative in which uracil in an oligonucleotide was substituted with C-5 propynyluracil, an oligonucleotide derivative in which uracil in an oligonucleotide was substituted with C-5 thiazoleuracil, an oligonucleotide derivative in which cytosine in an oligonucleotide was substituted with C-5 propynylcytosine, an oligonucleotide derivative in which cytosine in an oligonucleotide was substituted with phenoxazine-modified cytosine, an oligonucleotide derivative in which ribose in DNA was substituted with 2'-O-propylribose and an oligonucleotide derivative in which ribose in an oligonucleotide was substituted with 2'-methoxyethoxyribose. It is intended that a particular nucleic acid sequence also includes a variant thereof which was conservatively altered (e.g. a degenerate codon substituted body) and a complementary sequence thereof, like an explicitly shown sequence, unless otherwise indicated. Specifically, the degenerate codon substituted body can be attained by making a sequence in which the third position of one or more selected (or all) codons is substituted with a mixed base and/or deoxyinosine residue (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

As used herein, "nucleotide" may be naturally-occurring or non-naturally-occurring, as far as the objective function is retained.

An amino acid can be referred to herein, by either of the generally known three letters symbol thereof, or one letter symbol recommended by IUPAC-IUB Biochemical Nomenclature Commission. A nucleotide can be similarly referred by the generally recognized one letter code.

As used herein, "sugar chain" refers to a compound produced by connection of one or more sugar units (monosaccharide and/or derivative thereof). When two or more sugar units are connected, respective sugar units are bound by dehydration condensation with a glycoside bond. Examples of such a sugar chain include, but are not limited to, in addition to polysaccharides (glucose, galactose, mannose, fucose, xylose, N-acetylglucosamine, N-acetylgalactosamine, sialic acid as well as complexes and derivatives thereof), a variety of sugar chains degraded or derived from complex biomolecules such as degraded polysaccharides, glycoproteins, proteoglycans, glycosaminoglycans, and glycolipids. Therefore, as used herein, the sugar chain can be used interchangeably with "sugar", "polysaccharide", "glucide", and "carbohydrate". In addition, when not particularly referred, as used herein, "sugar chain" includes both of a sugar chain and a sugar chain-containing substance. Representatively, the sugar chain is a substance in which about 20 kinds of monosaccharides (glucose, galactose, mannose, fucose, xylose, N-acetylglucosamine, N-acetylgalactosamine, sialic acid as well as complexes and derivatives thereof) are connected in chains, and is attached to proteins or lipids inside or outside the cells of living bodies. The sugar chain is different in function depending on a sequence of a monosaccharide, and is usually complexly branched; it is predicted that there are several hundred kinds or more of sugar chains having various structures in the human body and, further, it is thought that there are several tens of thousands or more of types of structures useful in the human body. It is believed that the sugar chain is involved in the high order function served by proteins or lipids in living bodies, such as molecule/cell recognizing function between cells, but the majority of the mechanism is unknown. Sugar chains are studied in current life science as a third biological polymer next to nucleic acids and proteins. Inter alia, the function of the sugar chain as a ligand in cellular recognition (information molecules) is expected, and application thereof to the development of high-functional materials has been studied.

As used herein, "sugar chain group" is a name given when the sugar chain binds to another group. The sugar chain group refers to monovalent or divalent groups depending on the case. Examples of the sugar chain group include a sialyl Lewis X Group, an N-acetyllactosamine group, and an α1-6 mannobiose group.

Among abbreviations of the sugars as used herein, Neu5Ac is N-acetylneuraminic acid, Gal is galactose, GlcNAc is N-acetylglucosamine, GalNAc is N-acetylgalactosamine, and R is a non-sugar part (e.g. peptide, protein, lipid etc.).

Particular names of sugar chains are defined as follows.
2,3ST6G: Neu5Acα2→3Galβ1→3[GlcNAcβ1→6]GalNAcα-R,
2,3ST6L: Neu5Acα2→3Galβ1→3[Galβ1→4GlcNAcβ1→6]GalNAcα-R
2,3ST6SL: Neu5Acα2→3Galβ1→3[Neu5Acα2→3Galβ1→4GlcNAcβ1→6]GalNAcα-R
2,3ST: Neu5Acα2→3Galβ1→3GalNAcα-R
STn: Neu5Acα2-6GalNAcα-R
ST2-6: Galβ1→3[Neu5Acα2→6]GalNAcα-R
dST: Neu5Acα2→3Galβ1→3[Neu5Acα2→6]GalNAcα-R
Tn: GalNAcα-R
T: Galβ1→3GalNAcα-R As used herein, "homology" of a gene refers to a degree of identity of 2 or more gene sequences to each other. Therefore, as homology of 2 genes is higher, identity or similarity of those sequences is higher. Whether two kinds of genes have homology or not can be investigated by direct comparison of sequences, or in the case of a nucleic acid, by a hybridization method under the stringent conditions. When two gene sequences are directly compared, in the case where a DNA sequence is representatively at least 80% identical, preferably at least 90% identical, and more preferably at least 95% identical between the gene sequences, those genes have homology.

In the present invention, comparisons of similarity, identity and homology of amino acid sequences and nucleotide sequences are calculated using default parameters employing the BLAST tool for sequence analysis. Retrieval of identity can be performed, for example, using BLAST 2.2.9 of NCBI (issued on May 12, 2004). The value of identity as used herein usually refers to a value when alignment is performed under the default conditions using the BLAST, provided that when a higher value is obtained by change in a parameter, the highest value is adopted as a value of identity. When identity is assessed in a plurality of regions, the highest value among values is adopted as a value of identity.

As used herein, a "corresponding" gene refers to a gene which has, or is predicted to have the same action as that of a predetermined gene in a species as a standard of comparison, in a certain species and, when there are a plurality of genes having such an action, refers to a gene having the evolutionally same origin. Therefore, a gene corresponding to a certain gene (e.g. MUC1) can be the orthologue of the gene. Therefore, a gene corresponding to a human gene can be also found in other animals (mouse, rat, pig, rabbit, guinea pig, horse, sheep etc.). Such a corresponding gene can be identified using techniques well known in the art. Therefore, for example, a corresponding gene in a certain animal can be found by retrieving a sequence database of the animals (mouse, rat, pig, rabbit, guinea pig, horse, sheep etc.) and using a sequence of a gene as a standard for the corresponding gene as a query sequence.

As used herein, "fragment" refers to a polypeptide or a polynucleotide having a sequence length of 1 to n−1 relative to a full length polypeptide or polynucleotide (length is n). The length of the fragment can be appropriately changed depending on the purpose thereof, and examples of a lower limit of the length, in the case of the polypeptide, includes 3, 4, 5, 6, 7, 8, 9, 10, 15, 20, 25, 30, 40, 50 and more amino acids, and any length represented by an integer not specifically listed herein (e.g. 11 etc.) can be also suitable as the lower limit. In the case of the polynucleotide, examples of a lower limit of the length includes 5, 6, 7, 8, 9, 10, 15, 20, 25, 30, 40, 50, 75, 100 and more nucleotides, and any length represented by an integer not specifically listed herein (e.g. 11 etc.) can be also suitable as the lower limit. As used herein, the lengths of the polypeptide and the polynucleotide can be represented by the number of amino acids or nucleic acids, respectively, as described above, but the aforementioned number is not absolute, and it is intended that the aforementioned number as the upper limit or the lower limit also includes numbers which are a few more or less (or 10% more or less, for example) than the number, as far as the same function is possessed. In order to express such an intention, as used herein, the intention is expressed by adding "about" before the number, in some cases. However, as used herein, it should be understood that the presence or absence of "about" does not influence the interpretation of the numerical value. As used herein, the length of a useful fragment can be determined as whether at least one function among the functions of a full length protein as a standard of the fragment is retained or not.

As used herein, "variant", "variant sequence" or "analog" refers to one in which a part is changed relative to the original substance such as a polypeptide or a polynucleotide. Examples of such a variant include a substitution variant, an addition variant, a deletion variant, a truncated variant, and an allelic variant. The allele refers to genetic variants which belong to the same locus, and are discriminated from each other. Therefore, "allele variant" refers to a variant which is in a relationship of an allele relative to a certain gene. "Homolog" refers to one having homology (preferably, 80% or more homology, more preferably, 90% or more homology) with a certain gene at an amino acid level or a nucleotide level, in a certain species. A method of obtaining such a homolog is apparent from the description of the present specification.

In the present invention, in order to make a functionally equivalent polypeptide, addition, deletion or modification of an amino acid in addition to substitution of an amino acid can be also performed. Substitution of an amino acid refers to substitution of the original peptide with 1 or more, for example, 1 to 10, preferably 1 to 5, more preferably 1 to 3 amino acids. Addition of an amino acid refers to addition of 1 or more, for example, 1 to 10, preferably 1 to 5, more preferably 1 to 3 amino acids to the original peptide chain. Deletion of an amino acid refers to deletion of 1 or more, for example, 1 to 10, preferably 1 to 5, more preferably 1 to 3 amino acids from the original peptide. Amino acid modification includes, but is not limited to, amidation, carboxylation, sulfation, halogenation, alkylation, phosphorylation, hydroxylation, and acylation (e.g. acetylation). An amino acid to be substituted or added may be a naturally-occurring amino acid, a non-naturally-occurring amino acid, or an amino acid analog, and a naturally-occurring amino acid is preferable.

A nucleic acid encoding such a polypeptide can be obtained by a well-known PCR method, or can be chemically synthesized. These methods may be combined, for example, with a site-specific mutagenesis method, or a hybridization method.

As used herein, "substitution, addition and/or deletion" of a polypeptide or a polynucleotide refers to substitution, addition, or removal of an amino acid or a substitute thereof, or a nucleotide or a substitute thereof, respectively, relative to the original polypeptide or polynucleotide. The technique of such substitution, addition, and/or deletion is well-known in the art, and examples of such techniques include a site-specific mutagenesis technique. These changes in a nucleic acid molecule or a polypeptide as a standard can be generated at a 5' end or a 3' end of this nucleic acid molecule, or can be generated at an amino terminal or a carboxy terminal of an amino acid sequence indicating this polypeptide, or can be generated anywhere between those end sites, and can be individually scattered between residues in a standard sequence, as far as the objective function (e.g. binding to MUC1 in an anti-MUC1 antibody, an antigen-binding fragment thereof or a MUC1-binding molecule) is retained. Substitution, addition, or deletion may be any number as far as the number is 1 or more, and such a number is not limited, as far as the objective function (e.g. binding to MUC1) is retained in a variant having the substitution, the addition or the deletion. For example, such a number can be 1 or a few, preferably within 5% of the whole length, or 25 or less.

As used herein, "similar amino acid" refers to an amino acid in a relationship of conservative substitution, and the following amino acids correspond thereto. It is understood that variants in which the following substitution was performed also fall within the scope of the present invention, from the particular sequence (e.g. 12D10) of the present invention.

A: G, I, V, L
C: M (S-containing amino acid)
D: N, Q or E
E: N, Q or D
F: Y, A etc.
G: A
H: W etc.
I: A, L, V, (G)
K: R
L: A, I, V, (G)
M: S etc.
N: E, D or Q
P: HyP
Q: N, E or D
R: K
S: T, Y
T: S, Y
V: I, L, A, (G)
W: H
Y: F, S, T Substitution between these amino acids is also referred to as "conservative substitution".

As used herein, "amount" of a cancer-associated structure of MUC1 in a biological sample refers to a scale (e.g. molar weight, weight, etc.) that directly indicates the amount of substance of a target substance; and "level" of a cancer-associated structure of MUC1 in a biological sample refers to another scale (e.g. a scale that may be represented by an indicator (e.g. absorbance or the like) other than the amount in immunologically procedures) reflecting the amount of substance of a target substance. For the level or the like of a cancer-associated structure of MUC1 in a biological sample, the amount may be directly measured using a physicochemical procedure or the like, or the amount may be indirectly measured using an immunological procedure or the like. Alternatively, even if the amount is unknown, representation with a level reflecting an abundance (e.g. a level that may be represented by an indicator other than the amount using an immunological procedure) allows screening to be performed.

As used herein, "healthy individual" refers to a normal and healthy human, or a human who is confirmed not as contracting a cancer.

As used herein, "MUC1" refers to a protein of mucin 1 which is one type of mucin, or a gene, DNA or a nucleic acid thereof. It is a tumor-associated antigen, and is a high molecular weight glycoprotein which is expressed by many adenocarcinomas. It is taught that, in this protein, an extracellular domain of an indispensable membrane glycoprotein is mainly constituted by 30 to 90 tandem-type repeats of a 20 amino acid core sequence (as used herein, hereinafter also referred to as "Tn20-mer"; HGVTSAPDTRPAPGSTAPPA (SEQ ID NO.: 1)) rich in serine, threonine and proline. The repetition number of Tn20-mer expressed is genetically determined by an individual, resulting in size polymorphisms.

(Antibody)

As used herein, "antibody" collectively refers to a protein which is produced in a living body by stimulation with an antigen and specifically binds to or reacts with an antigen, in an immune reaction, or proteins having the same sequence thereto, which were produced by chemical synthesis, etc. The antibody is actually an immunoglobulin, and is also referred to as Ab.

As used herein, "antigen-binding fragment" of an antibody refers to, regarding a certain antibody, a fragment having a binding property to the same antigen as an antigen of the antibody. Whether the antibody falls into the scope of such "antigen-binding fragment" or not can be assessed by an affinity assay described as used herein. As used herein, such affinity can be indicated using a concentration at which a binding amount of a labeled MUC1 molecule to an antibody is 50% inhibited ($IC_{50}$ value) as an index, and the $IC_{50}$ value can be calculated, for example, by a regression model based on a logistic curve (Rodbard et al., Symposium on RIA and related procedures in medicine, P165, Int. Atomic Energy Agency, 1974).

As used herein, "MUC1-binding molecule" refers to any molecule which can bind to a MUC1 antigen either alone or in connection with other molecules. Therefore, it is understood that the MUC1-binding molecule includes binding molecules (aptamer or the like) other than an antibody and an antigenic binding fragment or the like of an antibody, other molecules (e.g. antibody complex molecule, antigenic binding fragment complex molecule or aptamer binding molecule) containing a binding part of an antibody and an antigenic binding fragment or the like of an antibody, or the like. Such a binding reaction can be determined by the same test as that of affinity of an antibody. As used herein, "antibody complex molecule" or "antigenic binding fragment complex molecule" refers to a molecule in which an antibody or an antigenic binding fragment binds to another molecule (e.g. protein, peptide, nucleotide, sugar, lipid and the like). Preferably, the antibody complex molecule or antigenic binding fragment complex molecule retains the binding ability of the original antibody complex molecule or antigenic binding fragment.

As used herein, "anti-MUC1 antibody" and "MUC1 antibody" are replaceably used, and they refer to an antibody which was raised against MUC1, or has a binding ability equivalent thereto.

As used herein, "antibody-dependent cytotoxicity" refers to the ability to kill a cell depending on an antibody. In order to measure this ability, for example, a chromium release test, etc. described herein can be used.

As used herein, "normal tissue-associated structure" refers to a structure which is highly expressed in a normal cell or a normal tissue which has not become cancerous (e.g. sugar chain structure). It is known that, in this structure, an expression amount is low in a cancer tissue or a cancer cell. Examples of a sugar chain of such a normal tissue-associated structure include
Neu5Acα2→3Galβ1→3[GlcNAcβ1→6]GalNAcα-R,
Neu5Acα2→3Galβ1→3[Galβ1→4GlcNAcβ1→6]GalNAcα-R(2,3ST6L) and
Neu5Acα2→3Galβ1→3
[Neu5Acα2→3Galβ1→4GlcNAcβ1→6]GalNAcα-R(2,3ST6SL).

As used herein, "cancer-associated structure" refers to a structure which is highly expressed in a cancer tissue or a cancer cell (e.g. sugar chain structure). It is known that, in this structure, an expression amount is low in normal tissue or a normal cell. Examples of a sugar chain of such a cancer-associated structure include Neu5Acα2-6GalNAcα-R <corresponding to STn(compound 4)>, Galβ1→3[Neu5Acα2→6]GalNAcα-R <corresponding to ST2-6 (compound 10)>, Neu5Acα2→3Galβ1→3[Neu5Acα2→6]GalNAcα-R <corresponding to dST (compound 11)>, Neu5Acα2→3Galβ1→3GalNAcα-R(2,3ST), GalNAcα-R (Tn) and Galβ1→3GalNAcα-R(T). Herein, Neu5Ac is N-acetylneuraminic acid, Gal is galactose, GlcNAc is N-acetylglucosamine, GalNAc is N-acetylgalactosamine, and R is a non-sugar part.

As used herein, "specificity" for a cancer-associated structure as compared with a normal tissue-associated structure refers to a nature of higher affinity to the cancer-associated structure as compared with the normal tissue-associated structure.

Such specificity can be expressed by a difference in cross reactivity. The cross reactivity is obtained by a calculation equation of ($IC_{50}$ for cancer-associated structure STn/$IC_{50}$ for sugar chain structure to be compared)×100(%). As used herein, inclusion of specificity refers to a difference of 2 fold or more. Alternatively, in directly comparing a difference in cross reactivity, the difference in cross reactivity can be, for example, about 2 fold or more, about 3 fold or more, about 4 fold or more, about 5 fold or more, about 10 fold or more, about 20 fold or more, about 30 fold or more, about 40 fold or more, about 50 fold or more, or even more. Herein, in a specific embodiment, specificity can be compared with a difference in cross reactivity of said normal tissue-associated structure to a cancer-associated structure, Neu5Acα2→6GalNAcα-R, of MUC1.

Alternatively, such specificity can be compared by evaluating specificity with fluorescence signal shift in a binding evaluation of cells by FACS. For example, in a specific embodiment, when specificity is evaluated with fluorescence signal shift in a binding evaluation of cells by FACS, specificity for a T-47D cell can be about 2-fold or more, about 3-fold or more, about 4-fold or more, about 5-fold or more, about 10-fold or more, about 20-fold or more, about 30-fold or more, about 40-fold or more, about 50-fold or more, or even more, compared to the specificity for 184A1 cell.

In addition, as used herein, $IC_{50}$ is a 50% inhibition concentration, and refers to a necessary concentration for 50% inhibition of binding of a certain antibody with an antigen. An $IC_{50}$ value can be calculated by a regression model based on a logistic curve (Rodbard et al., Symposium on RIA and related procedures in medicine, P165, Int. Atomic Energy Agency, 1974).

As used herein, "cancer cell" is used in the same sense as that of a tumor cell, and refers to a malignant cell. Examples of a representative cancer cell which is a subject of the present invention include a MUC1-expressing cell. About 75% of solid tumors are known to express MUC1 abnormally. MUC1 are known to be expressed in 90% or more of breast cancer cases, in about 50% of prostatic cancer cases, and in a high percentage in ovarian cancer cases, colon and rectum cancer cases, lung cancer cases and pancreatic cancer cases. Specific examples of cancer cells that express MUC1 include, for example, a T-47D cell, which is a breast cancer cell, and a Calu-3 cell, which is a lung cancer cell.

As used herein, "normal cell" refers to a cell that has not become cancerous. Specifically, for example, 184A1 cell, which is a mammary epithelial cell known as a normal cell expressing MUC1, MDA-MB-231 cell and the like.

As used herein, "tandem repeat dependency" refers to a nature such that as the number of repeats of a tandem structure of MUC1 is more, an antibody more strongly binds thereto. Tandem repeat dependency can be represented by the ratio of affinity to Tn20-mer biotin and Tn100-mer biotin (a tandem structure in which Tn20-mer biotin is repeated five times). For example, according to the method described in the Examples, the tandem repeat dependency can be represented by a value of a ratio (A100/A20) of absorbance at 450 nm in the case of using Tn20-mer biotin (A20), and absorbance at 450 nm in the case of using Tn100-mer biotin (A100).

As used herein, "tandem repeat dependency is low" means reaction is possible regardless of the number of the tandem structure (even in a case of one). Specifically, it refers to a case where the value of said A100/A20 is 2 or less, and preferably 1.5 or less.

As used herein, immunoglobulin "heavy chain variable domain (VH)" and "light chain variable (VL) domain" are used in the sense usually used in the art. Immunoglobulin is such that two L chains (light chains) and two H chains (heavy chains) having the same fundamental structure are connected with an S—S bond, the H chains are connected so that two fragments of Fc (crystallizable fragment) on a C terminal side and Fab (antigen binding fragment) on an N terminal side are bent at the hinge part, and a Y letter form is taken as a whole. In both of the L chain and the H chain, a sequence of about 110 amino acids (about half the length of the L chain) from the N terminal is a sequence which is partially different depending on antigen specificity. This part is called a variable part (variable region, V part), both variable parts of the L chain and the H chain (VL, VH) are involved in determination of the antigen specificity. A part other than the variable part is almost constant for each class or subclass, and is called a constant part (constant region, C part). The constant part is such that the number of a polypeptide unit comprising about 110 amino acids (homologous unit) is one in the case of the L chain (CL), three in IgG, IgA, and IgD (CH1, CH2, CH3), and four in IgM and IgE in the case of the H chain, and each unit, or a region generated by binding with an opposite site is called a domain.

(Description of an Antibody Molecule, an Antigen-Binding Fragment, or a Binding Molecule)

As used herein, unless particularly other senses are indicated, any polypeptide chain of an antibody, etc. is described as having an amino acid sequence beginning at an N-terminal extremity and ending at a C-terminal extremity. When an antigen-binding site includes both of $V_H$ and $V_L$ domains, these can be positioned on the same polypeptide molecule; preferably, each domain can be positioned at a separate chain and, in this case, the $V_H$ domain is a part of a heavy chain of immunoglobulin, that is, an antibody or a fragment thereof, and $V_L$ is a part of a light chain of immunoglobulin, that is, an antibody or a fragment thereof.

Examples of "antibody or antigen-binding fragment" as used herein include an antibody and a chimeric antibody produced by a B cell or a hybridoma, a CDR transplantation antibody or a human antibody or any fragment thereof, for example, $F(ab')_2$ and a Fab fragment, a single chain antibody and a single domain antibody. Therefore, it is understood that examples of "MUC1-binding molecule" as used herein include these antibodies and chimeric antibodies produced by a B cell or a hybridoma, a CDR transplantation antibody or a human antibody or any fragment thereof, for example, $F(ab')_2$ and a Fab fragment, and a single chain antibody and a single domain antibody bound with other molecules.

The single chain antibody comprises variable domains of a heavy chain and a light chain of an antibody which covalently bind with a peptide linker comprising 10 to 30 amino acids, preferably 15 to 25 amino acids. For this reason, it is thought that the structure thereof does not include constant parts of a heavy chain and a light chain, and a small peptide spacer has lower antigenicity than that of a whole constant part. "Chimeric antibody" means an antibody in which the constant region(s) of a heavy chain or a light chain or both of them is (are) derived from a specific animal such as human, while the variable domains of both of a heavy chain and a light chain are derived from animals other than the specific animal, such as non-human (e.g. mouse), or derived from the specific animal such as human, but are derived from an antibody of another one of the specific animal, such as human antibody. "CDR transplantation antibody" means an antibody in which a hypervariable site region (CDR) is, in a case regarding a specific animal, derived from a donor antibody such as a non-specific animal (e.g. mouse when the specific animal is human) antibody or another specific animal antibody (e.g. human) antibody, while all or substantially all other parts of the immunoglobulin, for example, a constant region and a highly conserved part of a variable domain, that is, a framework region is derived from an acceptor antibody, for example, a specific animal (e.g. human)-derived antibody. However, the CDR transplantation antibody includes a few amino acids of a donor sequence in the framework region, for example, in a part of the framework region adjacent to a hypervariable region. "Humanized antibody" means an antibody in which all of constant and variable regions of both of a heavy chain and a light chain are derived from human, or substantially the same as a human-derived sequence, but are not necessarily derived from the same antibody, and include an antibody produced by a mouse in which genes of a mouse immunoglobulin variable part and a mouse immunoglobulin constant part are substituted with human counterparts, for example, those described in general terminology in EP Patent 0546073B1, U.S. Pat. No. 5,545,806 etc.

Therefore, a preferable antibody, an antigen-binding fragment thereof or a MUC1-binding molecule is such that variable domains of a heavy chain and a light chain are derived from human, and can have a sequence shown, for example, in a variant of SEQ ID NO.: 2, 3, 14 or 15 (e.g. variant including substitution/insertion, addition or deletion of one or a few amino acids can be exemplified, but is not limited thereto). The constant region domain also includes, preferably, a suitable human constant region domain, for example, domains described in Kabat E. A. et al., US Department of Health and Human Services, Public Health Service, National Institute of Health. A CDR region can be found by investigating homology by applying an amino acid sequence of a variable region to a database of amino acid sequences of antibodies produced by Kabat et al. ("Sequence of Proteins of Immunological Interest" US Dept. Health and Human Services, 1983). A variant of a sequence of the CDR region, with at least one addition/insertion, substitution or deletion is also included in the present invention, as far as it is within a range where the desired biological activity (e.g. binding activity or neutralizing activity) of the present invention is retained. In addition, examples thereof include a sequence having 90 to 100% homology with each CDR region.

As used herein, "titer" refers to an amount of an antibody binding to an antigen, which is contained in a unit volume of anti-serum, in a serum reaction. Actual measurement is performed by adding a constant amount of an antigen to a dilution series of anti-serum, and a measured value is expressed by a dilution multiple number at an end point at which a reaction is generated.

As used herein, "affinity" refers to a binding force between an antibody and its recognition substance. As used herein, affinity ($K_D$) is indicated using a dissociation constant of an antibody and its recognition substance such as an antigen as an index. A method of measuring affinity ($K_D$) is well-known to a person skilled in the art, and affinity can be also obtained, for example, using a sensor chip.

The framework used herein can include any kind of a framework region, and is preferably a human-derived framework. A suitable framework region can be selected by referring to the literature of Kabat E. A. et al. A preferable heavy chain framework is a human heavy chain framework and, for example, is a framework of an anti-MUC1 antibody shown in SEQ ID NO.: 2. It can be determined from a sequence shown in SEQ ID NO.: 2 by referring to the literature; and consists of sequences of FR1, FR2, FR3 and FR4 regions. By a similar method, an anti-MUC1 light chain framework can be determined from a sequence shown in SEQ ID NO.: 3 by referring to the literature, and comprises sequences of FR1', FR2', FR3' and FR4' regions.

In a preferable embodiment, the present invention also provides a MUC1-binding molecule including at least one antigen-binding site containing either of a first domain having substantially the same amino acid sequence as that of a framework of SEQ ID NO.: 2 ($V_H$ sequence of 12D10), or a second domain having substantially the same amino acid sequence as that of a framework of SEQ ID NO.: 3 ($V_L$ sequence of 12D10).

Monoclonal antibodies generated to all proteins which are naturally seen in human can be typically produced in a non-human system, for example, a mouse. As a direct result, when administered to a human, a heterogeneous antibody as produced by a hybridoma elicits an undesirable immunological response which is predominantly mediated with a constant part of heterogeneous immunoglobulin. This can limit the use of an antibody which cannot be administered over a long period of time. Therefore, use of a single chain, a single domain, a chimera, CDR transplantation, or particularly a human antibody which is predicted not to exhibit substantial allergy response when administered to human is particularly preferable.

A more preferable anti-MUC1 antibody of the present invention, an antigen-binding fragment thereof, or a MUC1-binding molecule is selected from antibodies including at least a) (i) an immunoglobulin heavy chain variable domain ($V_H$) containing a hypervariable site, CDR1, CDR2 and CDR3 in a sequence, wherein CDR1 has a sequence SHDMS (SEQ ID NO: 4) or a variant thereof, CDR2 has a sequence AINSDGDNTYYPDTMER (SEQ ID NO: 5) or a variant thereof, and CDR3 has a sequence LTLRNWYFDV (SEQ ID NO: 6) or a variant thereof, or a fragment thereof, and (ii) a constant part of a human heavy chain, or a fragment thereof, and b) (i) an immunoglobulin light chain variable domain containing a hypervariable site, CDR1', CDR2' and CDR3' in a sequence, wherein CDR1' has an amino acid sequence KSSQSLLYSTNQQNYLA (SEQ ID NO: 7) or a variant thereof, CDR2' has an amino acid sequence WASTRES (SEQ ID NO: 8) or a variant thereof, and CDR3' has an amino acid sequence QQYYRYPPT (SEQ ID NO: 9) or a variant thereof, and (ii) a constant part of a human light chain, or a fragment thereof, as well as their direct equivalents.

In addition, the anti-MUC1 antibody of the present invention, an antigen-binding fragment thereof or a MUC1-binding molecule can be selected from single chain-binding molecules including a) a first domain containing CDR1, CDR2 and CDR3 which are hypervariable regions, in a sequence, wherein the hypervariable region has an amino acid sequence shown in SEQ ID NO.: 2, b) a second domain containing a hypervariable region, CDR1', CDR2' and CDR3' in a sequence, wherein the hypervariable region has an amino acid sequence shown in SEQ ID NO.: 3, c) an antigen-binding site containing a peptide linker binding to either of an N-terminal extremity of the first domain and a C-terminal extremity of the second domain, or a C-terminal of the first domain and an N-terminal of a second domain, and their direct equivalents.

As is well known, a minor change such as deletion, addition, insertion or substitution of one amino acid or a plurality of amino acids makes it possible to produce a protein corresponding to the original protein having substantial identity.

As used herein, "direct equivalent" as described above means any molecule of any anti-MUC1 antibody, an antigen-binding fragment thereof or a MUC1-binding molecule, comprising (i) hypervariable regions CDR1, CDR2 and CDR3 having at least 80% or more homology, preferably at least 90% or more homology, more preferably at least 95% or more homology to a hypervariable region shown in SEQ ID NO.: 4, 5 or 6 as a whole, and (i) hypervariable regions CDR1', CDR2' and CDR3' have at least 80% or more homology, preferably at least 90% or more homology, more preferably at least 95% or more homology to a hypervariable region shown in SEQ ID NO.: 7, 8 or 9 as a whole. As used herein, a plurality of amino acid sequences, in the case where the sequences have at least 80% or more identical amino acid residues at similar positions when they are optimally aligned, have at least 80% or more homology to each other and, in this case, gaps or insertions in the amino acid sequences are counted as non-identical residues.

A constant part of a human heavy chain can be $\gamma_1$, $\gamma_2$, $\gamma_3$, $\gamma_4$, $\mu$, $\alpha_1$, $\alpha_2$, $\delta$ or $\epsilon$ type, preferably $\gamma$ type, more preferably $\gamma_1$ type, while a constant part of a human light chain can be κ or λ type (including $\lambda_1$, $\lambda_2$ and $\lambda_3$ subtypes), preferably κ type. Amino acid sequences of all these constant parts are provided by Kabat et al.

In a normal procedure, accordingly, (i) a DNA molecule encoding a heavy chain or a light chain or a fragment thereof of the single domain MUC1-binding molecule of the present invention, the single chain MUC1-binding molecule of the present invention, the anti-MUC1 antibody of the present invention, an antigen-binding fragment thereof or a MUC1-binding molecule, and (ii) a use of the DNA molecule of the present invention for producing the anti-MUC1 antibody of the present invention, an antigen-binding fragment thereof or a MUC1-binding molecule by a recombination means, are provided.

(Production of Antibody)

The antibody of the present invention can be produced using any method well known in the art. Examples of such a method are described in the examples, but are not limited thereto. First, immunization of an animal using an antigen allows production of an antibody.

Herein, preparation of the antigen includes a peptide of a part of an amino acid sequence of a part of MUC1 prepared by a recombinant DNA method or chemical synthesis, and a glycosylated peptide thereof. Such a method is exemplified in the examples. The resulting human MUC1 is mixed with an adjuvant, and is used as an antigen. Examples of the adjuvant include Freund complete adjuvant, and Freund incomplete adjuvant, and any of them may be mixed.

Regarding a monoclonal antibody, the spleen or a lymph node is collected from a mammal, and an antibody-producing cell obtained therefrom is fused with a myeloma cell, and thus a monoclonal antibody-producing hybridoma can be obtained. A method of cell fusion can be performed by a known method, and the hybridoma can be made, for example, according to the method of Koehler & Milstein (Nature, 256, 495-497 (1975)). In order to make a specific antibody recognizing the objective protein, the objective animal (e.g. mouse) is immunized according to the aforementioned method. A sufficient increase in blood titer is confirmed, and blood is taken, or a spleen cell is separated. A hybridoma producing a monoclonal antibody, particularly, a monoclonal antibody recognizing a C-terminal or a loop of the protein can be made by fusing the thus separated spleen cell and a myeloma cell. The spleen cell is derived from the immunized animal, preferably a mouse. The myeloma cell is derived from mammal, and is preferably a mouse myeloma cell. In fusion of cells, polyethylene glycol, etc. can be used. A desired hybridoma can be selected by screening and cloning the hybridoma obtained by fusion. In order to make a monoclonal antibody, the resulting hybridoma is cultured in vitro or in vivo. Preferably, the hybridoma is cultured in vivo. For example, in order to produce ascites containing mouse monoclonal, the hybridoma is administered into the abdominal cavity of a mouse. The monoclonal antibody can be easily purified from the produced ascites by a method known to a person skilled in the art. It is preferable to collect spleen cells from the immunized animal 3 to 10 days after final immunization, but is not limited thereto.

In order to obtain a hybridoma from the resulting immunized cell, a plasmacytoma cell and an immune cell producing an antibody are fused, for example, in the presence of Sendai virus and polyethylene glycol for the purpose of allowing cells to be subcultured, by the method described, for example, in "Experimental Manual for Molecular Cell Biology" (Nankodo Co., Ltd., Takeichi Horie at al., 1994) etc., and thus a hybridoma can be obtained. As the plasmacytoma cell to be used herein, it is desirable to use a plasmacytoma cell derived from an allogeanic homeothermic animal even if the animal is the same homeothermic animal, and, when fused with a spleen cell obtained from a mouse as an immunized animal, it is preferable to use a mouse myeloma cell. Any known plasmacytoma cell can be utilized.

The hybridoma is selected by HAT medium (hypoxanthine, aminopterin, thymidine-added medium) and, at a stage of conformation of a colony, binding of an antibody secreted in the culture supernatant and an antigen is investigated (screened), and thus a hybridoma producing the objective antibody can be obtained.

Examples of the screening method include various methods generally used in detecting an antibody, such as a spot method, an agglutination reaction method, a Western blot method, and an ELISA method and, preferably, the screening method is implemented according to the ELISA method using reactivity with a MUC1 glycopeptide as an index, regarding the culture supernatant of the hybridoma, for example, as exemplified in the examples. This screening makes it possible to screen the objective antibody-producing strain which specifically reacts with MUC1 having a sugar chain specific for a cancer cell.

Cloning of the objective antibody-producing strain obtained as the result of screening can be implemented by a normal limiting dilution method or a soft agar method. The cloned hybridoma can be cultured at a large scale in a serum medium or a serum-free medium, if necessary. According to this culturing, a desired antibody having a comparatively high purity can be obtained as the culture supernatant. Alternatively, the hybridoma is inoculated into the abdominal cavity of a mammal having compatibility with the hybridoma, for example, a mouse, and a desired antibody can be also recovered as mouse ascites at a large amount. The culture supernatant of the antibody-producing hybridoma of the present invention and the ascites of a mouse, etc. can be used as a crude antibody liquid as they are. In addition, these can be purified by subjecting to ammonium sulfate fractionation, salting out, a gel filtration method, ion exchange chromatography, or an affinity chromatography method according to the common method.

A polyclonal antibody is obtained by collecting blood, for example, from a mammal immunized with an immunogen. In the method, as the mammal to be immunized with an immunogen, rabbit, goat, sheep, mouse and rat are generally used.

An immunizing method can be performed, for example, by administering an immunogen to a mammal by intravenous, intracutaneous, subcutaneous, or intraperitoneal injection according to a general method. More specifically, for example, an immunogen is diluted with a physiological saline-containing phosphate buffer (PBS) or physiological saline to a suitable concentration, and the mixture is administered to a test animal a few times at a 2 to 3 week interval, optionally together with a normal adjuvant. When a mouse is used, single dose is around 50 to 100 µg per animal. Herein, the adjuvant refers to a substance which non-specifically enhances an immune reaction to an antigen when administered with an antigen. Examples of the adjuvant which is usually used include pertussis vaccine, and Freund's adjuvant. Collection of the blood of a mammal 3 to 10 days after final immunization makes it possible to obtain anti-serum. The anti-serum can be used as it is, or it can be purified, and also used as a polyclonal antibody.

Examples of a method of purifying a polyclonal antibody include a non-specific purification method and a specific purification method. The non-specific purification method is mainly for the purpose of obtaining an immunoglobulin fraction by a salting out method or an ion exchange chromatography method. Examples of the specific purification method include an affinity chromatography method using an immobilized antigen.

As used herein, "immunogen" used upon production of an antibody, when used as used herein, represents a substance having the ability to generate an immune response, or to cause an immune response in an organism. The immunogen used in production of the antibody of the present invention can be made using an activated hapten and a carrier protein by an active ester method described in Antibodies: A Laboratory Manual, (1989) (Cold Spring Harbor Laboratory Press), etc.

Alternatively, the antigen can also be made by other methods described in Antibodies: A Laboratory Manual, (1989) (Cold Spring Harbor Laboratory Press), etc., for example, a carbodiimide method, a glutaraldehyde method or a diazo method.

As "carrier protein" used upon production of an antibody as used herein, any of various proteins known to enhance antigenicity can be used. Examples thereof include synthetic polypeptides in addition to polymer substances such as bovine serum albumin (BSA), bovine thioglobulin (BTG), and keyhole limpet hemocyanin (KLH).

"Hapten" used upon production of an antibody as used herein is a partial or incomplete antigen. The hapten is mainly a low molecular weight substance, and it alone has no ability to stimulate production of an antibody, but when it is bound to a carrier protein by a chemical method or with a crosslinking agent and immunization is performed as an artificial antigen, an antibody to the hapten can be obtained. In the present invention, since it is thought that it is difficult to produce an antibody with a MUC1 glycopeptide alone, a complex with a carrier protein such as a heterogeneous protein or a synthetic polypeptide was usually prepared and it was used as an immunogen.

(Immunological Measurement Method)

As a single specific antibody to be used in the present immunological measurement method, a monoclonal antibody which can be stably supplied is desirable, but the single specific antibody is not limited thereto, and any molecule can be used. Hereinafter, the method is exemplified using the monoclonal antibody. A sandwich immunological measurement method including the steps of immobilizing an antibody (first monoclonal antibody) on a solid phase, and incubating the antibody with a sample containing an antigen; further adding a labeled second monoclonal antibody, and incubating the resulting mixture; and detecting a labeled antigen antibody complex produced in the mixture is exemplified. Alternatively, in the immunological measurement method of the present invention, a sample, a solid phased first monoclonal antibody and a labeled second monoclonal antibody may be incubated at the same time. As the sandwich immunological measurement method, all sandwich immunological measurement methods such as a sandwich radiation immunological measurement method (RIA method), a sandwich enzyme immunological measurement method (EIA method), a sandwich fluorescent immunological measurement method (FIA method), a sandwich light emitting immunological measurement method (CLIA method), a sandwich light emitting enzyme immunological measurement method (CLEIA method), an immunological chromatograph method based on a sandwich method, etc. can be applied. For quantitation, the RIA method and the EIA method are preferable As used herein, "cross reactivity" refers to immunological cross reactivity. When an antibody obtained by immunization with a certain antigen also exhibits a binding reaction with another antigen (associated antigen), this reaction is referred to as a cross reaction. When a reaction amount between the objective antigen and its antibody is used as a standard, a degree of a reaction amount between the associated antigen and its antibody can be indicated as cross reactivity. As used herein, representatively, when indicated by a relative value (%) of affinity of 1%, 2%, 3%, or 0.5%, 0.2%, or 0.1% etc., cross reactivity can be said to be low. As the value is lower, cross reactivity is lower, and it is indicated that specificity to the objective antigen is possessed. In many cases, cross reactivity occurs mainly due to high similarity between structures of the objective antigen and an associated antigen.

The anti-MUC1 antibody of the present invention, an antigen binding fragment thereof or a MUC1-binding molecule can be solid-phased on carriers such as microtiter plates, beads, tubes, membranes, filter paper, and plastic cups and, particularly, polyethylene beads are used. A sample to be measured can be a sample containing human MUC1 such as human plasma, serum, blood and urine. The anti-MUC1 antibody of the present invention, an antigen-binding fragment thereof or a MUC1-binding molecule can be labeled with a radioactive isotopic element, an enzyme, a fluorescent substance, a light emitting substance, or in a visual-determinable simple measurement method, with a gold colloid or a coloring latex etc. Examples of the radioactive isotopic element used in labeling include $^{14}C$, $^{3}H$, $^{32}P$, $^{125}I$, and $^{131}I$ and, particularly, $^{125}I$ is suitably used. These can be bound to a monoclonal antibody by a chloramine T method, a peroxidase method, an Iodogen method, or a Volt Hunter method etc. Examples of the enzyme which can be used in labeling include β-galactosidase (βGAL), alkaline phosphatase (ALP), and horseradish peroxidase (HRP). These can be bound to a monoclonal antibody by a periodic acid crosslinking method (Nakane method), or a method of Ishikawa et al. (Igaku-Shoin Ltd.; Enzyme Immunological Measurement Method, third edition, 75-127 (1987)), etc. Examples of the fluorescent substance used in labeling include fluorescein, fluorescamine, fluorescein isothiocyanate, and tetramethylrhodamine isothiocyanate. Examples of the light emitting substance used in labeling include luciferin, a luminol derivative, and an acridinium ester. In a simple measurement method etc., a gold colloid or a coloring latex may be used.

According to one embodiment of the present invention, a sandwich RIA method can be performed. In the sandwich RIA method, specifically, a bead solid-phased with a first monoclonal antibody is added to a standard solution or a sample, and they are mixed, and incubated at 4° C. to 45° C. preferably 25° C. to 37° C. for 1 to 4 hours, preferably 2 hours (first reaction). After washing, a solution containing a second monoclonal antibody labeled, for example, with $^{125}I$ is added, and the mixture is incubated at 4° C. to 45° C., preferably 25° C. to 37° C. for 1 to 4 hours, preferably 2 hours to form an antibody/antibody complex on the bead (second reaction). After washing, radioactivity of the antigen antibody complex bound to the bead is detected with a gamma counter etc., and thus an amount can be measured. According to another preferable embodiment, a sandwich EIA method can be performed. In the sandwich EIA method, specifically, a bead on which a first monoclonal antibody is immobilized and is added to a standard solution or a sample, and they are mixed, and incubated at 4° C. to 45° C., preferably 25° C. to 37° C. for 1 to 4 hours, preferably 2 hours (first reaction). After washing, a solution containing a second monoclonal antibody labeled with an enzyme, for example, horseradish peroxidase (HRP) is added, and the mixture is incubated at 4° C. to 45° C., preferably 25° C. to 37° C. for 1 to 4 hours, preferably 2 hours to form an immunological complex comprising antibody-antibody on a bead (second reaction). The enzyme activity on the bead is measured by a colorimetric method via a substrate specific for an enzyme, for example, tetramethylbenzidine (TMB) when a labeling enzyme is HRP, and thus a captured amount on the bead can be measured. Colorimetric quantitation is performed with a normal spectral photometer.

In one embodiment of the present invention, the antigen binding ability can be measured as follows. In the case of Cell ELISA plate for measuring antigen binding, a sample is prepared as follows. Human breast cancer cell T-47D (ATCC HTB-133) is seeded into 60 wells of a 96-well plate for cell culturing at a cell number of $1\times10^6$. It is cultured with a $CO_2$ incubator for 1 day (RPMI1640 medium containing 10% bovine fetal serum (GIBCO)) to adhere cells. The culturing solution is discarded, and each well is washed with 300 µl of PBS two times. PBS (100 µl) containing 4% paraformaldehyde (hereinafter, referred to as PFA/PBS) is added to each well and it is allowed to stand on an ice for 10 minutes to solid-phase the cells. PFA/PBS is discarded, and each well is washed with 300 µl of PBS two times, followed by blocking with 250 µl of DB. To each well is added 100 µl of a MUC1 antibody, it is incubated at room temperature for 2 hours, and washed with RB and, thereafter, 100 µl of an alkaline phosphatase-bound second antibody which has been diluted 1000-fold with DB is added. It is incubated at room temperature for 1 hour, and washed with RB, thereafter, a substrate solution is added and, then, absorbance at 405/655 nm is measured with a microplate reader (Bio-Rad).

Neutralizing activity can be measured using antibody-dependent cytotoxicity as an index.

In one embodiment of the present invention, the antibody-dependent cytotoxicity can be measured as follows. That is, the antibody-dependent cytotoxicity can be analyzed by a chromium release test. Human peripheral mononuclear cell (PBMC) is separated from peripheral blood of a healthy subject using Ficoll-paque PLUS (manufactured by GE Healthcare) according to a package insert. DMEM containing 10% FCS is added so that the separated PBMC becomes $4 \times 10^6$/ml. Physiological saline containing $^{51}$Cr is added to DMEM containing $1 \times 10^6$ human breast cancer cell strains (e.g. T-47D) or human mammary gland epithelial cell strains (e.g. 184A1), followed by a reaction at 37° C. for 1 hour. Thereafter, it is appropriately washed with DMEM, and DMEM is added to a predetermined amount (e.g. $5 \times 10^4$/ml). To this cell is added 12D10 or mouse IgG2a (manufactured by SIGMA-ALDRICH) to react them at 37° C. for 1 hour, and it is added to a 9 well V-bottom plate so as to have a suitable amount (e.g. 100 µl/well). Thereafter, a suitable amount, for example, 100 µl of PBMC is added, followed by a reaction at 37° C. for 2 hours. Thereafter, the plate is centrifuged at 500×g for 5 minutes at room temperature, and γ-ray of 100 µl of the supernatant is measured with a measuring equipment (e.g. ARC-7001 (manufactured by Aloka Co., Ltd.)). Antibody-specific cytotoxicity (%) is obtained using the following calculation equation.

Cytotoxicity(%)=(experimental value−natural release)/(maximum release−natural release)×100

According to the technical level in the art, a person skilled in the art can make a humanized antibody, for example, by a CDR grafting method (e.g. EP 239400).

The present invention includes first and second DNA constructs for producing an antibody, an antigen-binding fragment thereof or a MUC1-binding molecule as described below.

The first DNA construct encodes a heavy chain or a fragment thereof, and includes a) a $V_H$ region encoding a variable domain containing a framework and a supervariable region, wherein the supervariable region is sequences of CDR1, CDR2 and CDR3, and an amino acid sequence thereof is shown in SEQ ID NO.: 4, 5 or 6; this $V_H$ region begins at a codon encoding a first amino acid of the variable domain, and ends at a codon encoding a last amino acid of the variable domain, and b) a heavy chain constant region beginning at a codon encoding a first amino acid of the constant region of a heavy chain and ending a codon encoding a last amino acid of the constant region thereof or a fragment thereof, or a fragment thereof and, followed by a stop codon.

For example, the first DNA construct encodes the aforementioned $V_H$ region, and the constant region of a human heavy chain, more preferably the constant region of a human γ1 chain. This constant region can be a DNA fragment (including intron) or a cDNA fragment (not accompanying an intron) derived from genome.

The second DNA construct encodes a light chain or a fragment thereof, and includes a) a VL region encoding a variable domain containing a framework and a hypervariable region, wherein the hypervariable region is CDR1', CDR2' and CDR3', and an amino acid sequence thereof is shown in SEQ ID NO.: 7, 8 or 9; this VL region begins at a codon encoding a first amino acid of the variable domain and ends at a codon encoding a last amino acid of the variable domain, and b) a light chain constant region beginning at a codon encoding a first amino acid of the constant region of a light chain, and ending at a codon encoding a last amino acid of the constant region thereof or a fragment thereof, or a fragment thereof, followed by a stop codon. Preferably, the constant region encodes the constant region of a human light chain, more preferably the constant region of a human κ chain.

The present invention also includes an anti-MUC1 antibody in which one or more residues of CDR1, CDR2, CDR3, CDR1', CDR2' or CDR3' are derived from a residue shown in SEQ ID NO.: 2, for example, by mutation, for example, site-specific mutagenesis of a corresponding DNA sequence, an antigen-bounding fragment thereof or a MUC1-binding molecule. The present invention includes a DNA sequence encoding the altered anti-MUC1 antibody, an antigen-binding fragment thereof or a MUC1-binding molecule. Particularly, the present invention includes an anti-MUC1 antibody in which one or more residues of CDR1' or CDR2' are altered from a residue shown in SEQ ID NO.: 7 or 8, an antigen-binding fragment thereof or a MUC1-binding molecule.

In the first and second DNA constructs described above, first and second parts can be separated with an intron, and an enhancer can be usually positioned in an intron between the first and second parts. The presence of an enhancer which is transcribed, but is not translated, can assist effective transcription. In a particular embodiment, the first and second DNA constructs advantageously include an enhancer of a heavy chain gene of human origin.

The antibody of the present invention can be made as a chimeric antibody, and an expression vector of such a chimeric antibody, if a DNA fragment encoding an H chain V region is cloned, expresses DNA encoding these mouse V regions by connecting with DNA encoding a human antibody constant region, and thus a chimeric anti-human antibody is obtained. A fundamental method for making the chimeric antibody comprises connecting a leader sequence and a V region sequence present in a cloned cDNA to a sequence encoding a human antibody C region already present in an expression vector of a mammal cell. Alternatively, the method comprises connecting a mouse leader sequence and a V region sequence present in a cloned cDNA to a sequence encoding a human antibody C region and, thereafter, connecting the resultant to an expression vector of a mammal cell.

A fragment of a human antibody C region can be of a H chain C region of any human antibody and a L chain C region of a human antibody, and examples thereof include Cγ1, Cγ2, Cγ3, or Cγ4 for a human H chain, and Cλ or Cκ for a L chain, respectively.

Each DNA construct is placed under control of a suitable controlling sequence, particularly, under control of a suitable promoter. Any kind of a promoter can be used, provided that it is applied to a host organism to which the DNA construct has been transferred for expression. For producing the chimeric antibody, an expression vector including DNA encoding a mouse H chain V region and a human H chain C region under an expression controlling region such as an enhancer/ promoter system, as well as a single expression vector including DNA encoding a mouse L chain V region and a human L chain C region under control with an expression controlling region such as an enhancer/promoter system (e.g. see WO 94/11523) are made. Then, a host cell such as a mammal cell is co-transformed with this expression vector, and the transformed cell is cultured in vitro or in vivo to produce a chimeric antibody (e.g. see WO 91/16928).

A desirable antibody can be produced during cell culturing or in a transgenic animal. A suitable transgenic animal can be obtained according to a standard method including micro-injecting first and second DNA constructs to be placed under a suitable controlling sequence into an egg, transferring a prepared egg into a pseudopregnant female, and selecting an offspring expressing a desirable antibody.

When an antibody chain is produced during cell culturing, the DNA construct needs to be inserted first into a single expression vector, or into compatible expression vectors although they are separate two vectors, and the latter case is more preferable.

Accordingly, the present invention also provides an expression vector which can be replicated in a prokaryotic system or a eukaryotic system, the vector including at least one DNA construct of the aforementioned DNA constructs.

Then, each expression vector including the DNA construct is transferred into a suitable host organism. When the DNA constructs are inserted into two expression vectors separately, they can be transferred separately, that is, with one-type vector per cell, or co-transferred. The suitable host organism is a microorganism, yeast or a mammal cell system, and the latter is preferable. More preferably, the mammal cell system is lymphocyte-derived, for example, myeloma, hybridoma or a normal immortalized B cell, and they usually do not express any endogeneous antibody heavy chain and light chain.

Accordingly, the anti-MUC1 antibody of the present invention, an antigen-binding fragment thereof or a MUC1-binding molecule can be made by (i) culturing an organism transformed with the aforementioned expression vector, and (ii) recovering an anti-MUC1 antibody, an antigen-binding fragment thereof or a MUC1-binding molecule from the culture.

In order to purify DNA and determine a nucleotide sequence, the following method can be used. Regarding a PCR product, agarose gel electrophoresis is performed according to a known procedure, the objective DNA fragment is excised, recovery and purification of DNA are performed and the DNA is ligated to a vector DNA. Purification of the DNA is performed by extracting the DNA with phenol and chloroform (J. Sambrook, at al. "Molecular Cloning", Cold Spring Harbor Laboratory Press, 1989), or using a commercially available kit (e.g. GENECLEAN II; BI0101). As vector DNA for retaining a DNA fragment, a known vector (e.g. pUC19, Bluescript etc.) can be used.

Such DNA and vector DNA are ligated using a known ligation kit (manufactured by TAKARA SHUZO CO., LTD.) to obtain a recombinant vector. Then, the resulting recombinant vector is introduced into an *Escherichia coli* JM109 competent cell (Nippon Gene Co., Ltd.) etc., and then an ampicillin-resistant colony is selected, and vector DNA is prepared based on a known method (J. Sambrook, et al. "Molecular Cloning", Cold Spring Harbor Laboratory Press, 1989). A nucleotide sequence of the objective DNA is determined by a known method (e.g. dideoxy method) after digestion of the vector DNA with a restriction enzyme (J. Sambrook, et al. "Molecular Cloning", Cold Spring Harbor Laboratory Press, 1989). In the present invention, an automatic nucleotide sequence determining apparatus (e.g. DNA Sequencer 373A, Applied Biosystems) can be used.

The present inventions can be also provided as a humanized antibody. For making such a humanized antibody, first, retrieval of homology with a human antibody is performed.

That is, in order to make a humanized antibody in which CDR of a mouse monoclonal antibody is transplanted into a human antibody, it is desirable that there is high homology between FR of the mouse monoclonal antibody and FR of the human antibody. Therefore, V regions of an H chain and an L chain of a mouse anti-human TF monoclonal antibody are compared with V regions of all known antibodies, structures of which have been elucidated using a database. At the same time, the comparison with human antibody subgroups (HSG: Human subgroup) which were classified by a length of FR of an antibody, homology of amino acids etc. by Kabat et al. (Kabat, E. A. et al., US Dep. Health and Human Services, US Government Printing Offices, 1991) is performed.

In the case of a human H chain V region, the region can be classified into HSGI to III by HSG classification of Kabat et al. On the other hand, a human L chain K chain V region can be classified into HSGI to IV by HSG classification of Kabat et al.

When a mouse antibody is humanized by a conventional art, if necessary, in order to make the structure of CDR of a humanized V region further approach the structure of the original mouse antibody, an amino acid sequence of a part of FR in a V region of a mouse antibody supporting CDR is transplanted into FR in a human V region, in some cases. However, regarding which amino acid of FR in a V region of a mouse antibody should be transplanted into FR in a human antibody V region, there is no constant rule. Therefore, it is presumed that specification of essential amino acids for retaining the structure of CDR needs many efforts, while when the CDR is specified, constant binding specificity is possessed, and therefore in the present invention, it is understood that in the case of possession of a sequence of CDR included in 12D10, other sequences may be changed.

(Medicament)

Although the antibody of the present invention can be administered alone as it is, it is usually preferably provided as various pharmaceutical preparations. In addition, those pharmaceutical preparations are used in animals and human.

An effective dose and an administration time of the antibody of the present invention are different depending on an administration form, the age and weight of a patient, the nature or severity of symptoms to be treated etc. A dose is usually 0.01 to 100 mg per 1 kg weight per time, preferably 5 to 50 mg per 1 kg weight per time. It is preferable that regarding an administration time, the antibody is administered once a day or by division.

(Assay, Detection and Diagnosis)

In one aspect, the present invention provides a method of diagnosing cancer (non-epithelial malignant inflammatory disease, adenocarcinoma, breast cancer, colorectal cancer, pancreas cancer, pulmonary adenocarcinoma, non-small cell lung cancer, ovarian cancer, stomach cancer, prostate cancer, endometrial cancer, and colorectal cancer) as well as cystic fibrosis, asthma, chronic obstructive pulmonary disease and the like, using the antibody of the present invention, an antigen-binding fragment thereof or a MUC1-binding molecule; a diagnosis agent including the antibody of the present invention, an antigen-binding fragment thereof or a MUC1-binding molecule; or a diagnosis kit including the antibody of the present invention, an antigen-binding fragment thereof or a MUC1-binding molecule. It is understood that the antibody of the present invention, an antigen-binding fragment thereof or a MUC1-binding molecule included in the diagnosis method, diagnosis agent or diagnosis kit of the present invention can be any embodiment of the antibody of the present invention, an antigen-binding fragment thereof or a MUC1-binding molecule described above. In particular, the antibody of the present invention, an antigen-binding fragment thereof or a MUC1-binding molecule specifically binds to a sugar chain structure expressed in specific cancers, and thus it can be used for diagnosis of these cancers.

In another aspect, the present invention provides an immunoassay using the antibody of the present invention, an antigen-binding fragment thereof or a MUC1-binding molecule. Alternatively, the present invention provides a method for detecting MUC1 or an associated molecule thereof, using the antibody of the present invention, an antigen-binding fragment thereof or a MUC1-binding molecule. Alternatively, the present invention provides a detection agent including the antibody of the present invention, an antigen-binding fragment thereof or a MUC1-binding molecule, or a detection kit including the antibody of the present invention, an antigen-binding fragment thereof or a MUC1-binding molecule. It is understood that the antibody, an antigen-binding fragment thereof or a MUC1-binding molecule included in the method for detecting cancer, detection agent or detection kit of the present invention may be any embodiment of the antibody of the present invention, an antigen-binding fragment thereof or a MUC1-binding molecule described above. Since the antibody of the present invention, an antigen-binding fragment thereof or a MUC1-binding molecule specifically binds to a sugar chain structure expressed in specific cancers, it can be used for detection of these cancers or tumor cells.

The antibody of the present invention, an antigen-binding fragment thereof or a MUC1-binding molecule can be a modified antibody in which a modifying agent is bound thereto in order to improve stability or an antibody titer. Examples of the modifying agent include polymers such as sugar chains, and polyethylene glycol (PEG), and the like.

In addition, the antibody of the present invention, an antigen-binding fragment thereof or a MUC1-binding molecule can be labeled. In this case, a labeled one can be used in immunoassay such as labeling immunoassay, including radioimmunoassay, enzyme immunoassay (e.g. ELISA), and fluorescent immunoassay. In the labeling immunoassay, many test samples can be analyzed at once and, furthermore, these assays are characteristic of little time and labor necessary for analysis while achieving analysis of high precision, as compared with bioassay.

In addition, an antibody which is generally used in diagnosis is made by immunizing an animal other than human, such as mouse, rabbit and goat. However, in the immune system of an animal, a lymphocyte producing an antibody which binds to a molecule constituting its own body is excluded or inactivated. That is, among the antibodies of the present invention which are made by immunizing an animal, antibodies in which a part very similar between that of human and that of an animal is an antigen determinant region, are not included.

The antibody of the present invention, an antigen-binding fragment thereof or a MUC1-binding molecule can be used as a marker for diagnosing cancers, or monitoring progression of a disease in a patient. In one embodiment, cancer of a patient can be diagnosed by assessing a biological sample obtained from the patient for a MUC1 level by comparison with a predetermined cutoff value. A suitable "biological sample" as used herein includes blood, serum, urine and/or cancer tissue secretion.

In the present invention, regarding use of a binding partner for detecting a polypeptide marker in a sample, there are various assay formats known to a person skilled in the art. For example, see Harlow and Lane, Antibodies: A Laboratory Manual, Cold Spring Harbor Laboratories, 1988. In an embodiment, an assay includes use of a binding partner immobilized on a solid phase support, for binding to a polypeptide from the residue of a sample, and removing the polypeptide. Then, the binding polypeptide can be detected employing a second binding partner including a reporter group. A suitable second binding partner includes an antibody which binds to a binding partner/polypeptide complex. Alternatively, a competitive assay can be utilized, wherein a polypeptide is labeled with a reporter group, and can bind to a binding partner which was immobilized after incubation of the binding partner and the sample. The degree of inhibition of binding a labeled polypeptide to a binding partner by a sample component is an index of reactivity between the sample and the immobilized binding partner.

A solid phase support used herein can be any substance known to a person skilled in the art, to which an antigen can be attached. For example, the solid phase support can be a test well of a microtiter plate, or nitrocellulose or other suitable membranes. Alternatively, the support can be a bead or a disk (e.g. glass, fiberglass, latex, or plastic substance such as polystyrene or polyvinyl chloride). The support can be also a magnetic particle or an optical fiber sensor as disclosed, for example, in U.S. Pat. No. 5,359,681. A binding factor can be immobilized on a solid phase support, using various techniques known to a person skilled in the art (these are sufficiently described in patents and scientific literature). In the situation of the present invention, the term "immobilization" refers to both non-covalent association (e.g. adsorption) and covalent attachment (this can be direct binding between an antigen and a functional group on a support, or binding via a crosslinking agent). Immobilization in a well in a microtiter plate or on a membrane by adsorption may be used. In such a case, adsorption can be attained by contacting a binding factor with a solid phase support in a suitable buffer for a suitable amount of time. The contact time can vary with temperature, and is representatively from about 1 hour to about 1 day. Contact between a well of a microtiter plate made of a plastic (e.g. polystyrene or polyvinyl chloride), and a binding factor in an amount within a range of about 10 ng to about 10 μg, preferably about 100 ng to about 1 μg is sufficient for immobilizing a suitable amount of the binding factor.

In the present invention, covalent attachment of the binding factor to the solid phase support can be generally attained by first reacting a bifunctional reagent which reacts with both of the functional groups (e.g. hydroxyl or amino group) the binding factor and the support. For example, the binding factor can be covalently attached to a support having a suitable polymer coating, by use of benzoquinone, or condensation between an aldehyde group on the support and amine and active hydrogen on the binding partner (e.g. see Pierce Immunotechnology Catalog and Handbook, 1991 A12-A13).

In a certain embodiment, the assay is a two antibody sandwich assay. This assay can be performed by first contacting an antibody immobilized on a solid phase support (usually, a well of microtiter plate) and a sample, thereby binding a polypeptide in the sample to an immobilized antibody. Then, an unbound sample is removed from an immobilized polypeptide-antibody complex, and a second antibody (including a reporter group) which can bind to a different site on the polypeptide is added. Then, an amount of the second antibody which remains bound to the solid phase support is determined using a method suitable for a particular reporter group.

More specifically, when an antibody is once immobilized on a support as described above, a protein-binding site remaining on the support is representatively blocked. Any suitable blocking reagent known to a person skilled in the art is, for example, bovine serum albumin or Tween 20™ (Sigma Chemical Co., St. Louis, Mo.). Then, the immobilized antibody is incubated with the sample, and the polypeptide can be bound to an antibody. The sample can be diluted with a suitable diluent such as phosphate-buffered saline (PBS) before incubation. Generally, a suitable contact time (i.e. incubation time) is a sufficient period of time for detecting the presence of the polypeptide in the sample obtained from an individual having cancer. Preferably, the contact time is sufficient for attaining a level of binding which is at least about 95% of a level which is attained in equilibrium between a bound polypeptide and an unbound polypeptide. A person skilled in the art recognizes that a necessary time for reaching equilibrium can be easily determined by assaying a level of binding which is generated over time. At room temperature, an incubation time for about 30 minutes is generally sufficient.

Subsequently, an unbound sample can be removed by washing the solid phase support with a suitable buffer (e.g. PBS containing 0.1% Tween 20™). Then, a second antibody including a reporter group can be added to the solid phase support. Examples of the reporter group include an enzyme (e.g. horseradish peroxidase), a substrate, a cofactor, an inhibitor, a dye, a radioactive nuclide, a light emitting group, a fluorescent group and biotin. Binding of the antibody to the reporter group can be attained using a standard method known to a person skilled in the art.

Subsequently, the second antibody is incubated with the immobilized antibody-polypeptide complex for a sufficient amount of time for detecting the bound polypeptide. The suitable amount of time can be generally determined by assaying a level of binding generated over a time. Then, an unbound second antibody is removed, and a bound second antibody is detected by using the reporter group. A method used for detecting the reporter group depends on the nature of the reporter group. For a radioactive group, a scintillation counting method or an autoradiography method is generally suitable. A spectroscopic method can be used for detecting a dye, a light emitting group and a fluorescent group. Biotin can be detected using avidin bound to a different reporter group (usually, radioactive group or fluorescent group or enzyme). The reporter group of an enzyme can be detected by addition of a substrate (generally, for a particular time), followed by spectroscopic analysis or other analysis of the reaction product.

For detecting the presence or absence of cancer, a signal detected from a reporter group which remains bound to the solid phase support is generally compared with a signal corresponding to a predetermined cutoff value. In one embodiment, the cutoff value is an average of signals obtained when an immobilized antibody is incubated with a sample from a patient having no cancer. Generally, samples generating signals which are three standard deviations exceeding the predetermined cutoff value are thought to be positive for cancer. In another embodiment, the cutoff value is determined using Receiver Operator Curve according to the method of Sackett et al., Clinical Epidemiology: A Basic Science for Clinical Medicine, Little Brown and Co., 1985, pp 106-7. Simply, in this embodiment, the cutoff value can be determined from plotting of a set of a true positive ratio (i.e. sensitivity) and a pseudopositive ratio (100%-specificity) corresponding to respective possible cutoff values of the result of a diagnostic test. A cutoff value on a plot nearest an upper part left corner (i.e. a value covering the maximum region) is the most precise cutoff value, and a sample generating a higher signal than the cutoff value determined by the method of the present invention is thought to be positive. Alternatively, a cutoff value can be shifted left for minimizing a pseudopositive ratio, or can be shifted right for minimizing a pseudonegative ratio, along a plot. Generally, a sample generating a higher signal than the cutoff value determined by the present method is determined to be positive for the cancer.

In a related embodiment, an assay is carried out in a flow-through or test strip format, wherein an antibody is immobilized on a membrane (e.g. nitrocellulose). In the flow-through test, when a sample passes through the membrane, a polypeptide in the sample binds to an immobilized antibody. Then, when a liquid containing a second antibody passes through the membrane, the second labeled antibody binds to an antibody-polypeptide complex. Then, detection of the bound second antibody can be carried out as described above. In the strip test format, one end of the membrane to which the antibody binds is immersed in a solution containing a sample. The sample moves along a membrane passing a region containing the second antibody, and to a region of an immobilized antibody. A concentration of the second antibody in the region of an immobilized antibody shows the presence of cancer. Representatively, the concentration of the second antibody at this site forms a pattern (e.g. line), and this can be visually read. The absence of such a pattern shows a negative result. Generally, an amount of the immobilized antibody on the membrane, when a biological sample contains a sufficient level of a polypeptide for generating a positive signal in a two antibody sandwich assay in the aforementioned format, is selected so that a pattern which can be visually recognized is generated. Preferably, an amount of the immobilized antibody on the membrane is in a range of about 25 ng to about 1 µg, more preferably about 50 ng to about 500 ng. Such a test can be representatively carried out with a very small amount of a biological sample.

As a matter of course, there are many other assay protocols suitable for the antibody of the present invention or use of the antibody. It is intended that the aforementioned description is mere exemplification.

The present invention also relates to a system, an apparatus or a kit for manufacturing the pharmaceutical composition or assay kit of the present invention. It is understood that as constitutional requirements of such a system, apparatus or kit, those known in the art can be utilized, and a person skilled in the art can appropriately design them.

The present invention also relates to a system, an apparatus or a kit using the compound of the present invention, a pharmaceutically acceptable salt thereof, or a prodrug thereof such as a hydrate, etc. It is understood that as constitutional requirements of such a system, apparatus or kit, those known in the art can be utilized, and a person skilled in the art can appropriately design them.

The reference documents such as scientific documents, patents and patent applications cited as used herein are incorporated by reference as used herein to the same degree that a whole thereof is specifically described, respectively.

Hereinafter, the present invention will be described based on examples, but the following examples are provided only for the purpose of exemplification. Therefore, the scope of the present invention is not limited to the aforementioned embodiments or the following example, but is limited only by the attached claims.

EXAMPLES

Hereinafter, the present invention will be described in more detail by way of examples, but the technical scope of the present invention is not limited by the examples, etc. Reagents, resins, etc. used in the following examples can be obtained from Wako Pure Chemical Industries, Ltd., Sigma-Aldrich, etc. unless otherwise is indicated.

Abbreviations used in the present examples have the following meanings.
DMF: N,N-dimethylformamide
DCM: Dichloromethane
HBTU: 1-[Bis(dimethylamino)methylene]-1H-benzotriazolium-3-oxide hexafluorophosphate
HOBt: N-hydroxybenzotriazole
DIEA: Diisopropylethylamine
Fmoc: (9H-fluoren-9-yl)methoxycarbonyl
TIS: Triisopropylsilane
CMP-NANA: Disodium cytidine-5'-monophospho-N-acetylneuraminate
UDP-Gal: Disodium uridine-5'-diphospho-N-galactose In a reaction under microwave irradiation in the present examples, a microwave-type organic chemistry synthesis apparatus Green Motif I (manufactured by Tokyo Electronic Co., Ltd.) was used.

Example 1

Synthesis of MUC1 Tn20-Mer Glycopeptide

Synthesis of Example Compound 1

H-His-Gly-Val-Thr-Ser-Ala-Pro-Asp-<u>Thr</u>(Galβ1→

3GalNAcα)-Arg-Pro-Ala-Pro-Gly-Ser-Thr-Ala-Pro-

Pro-Ala-NH$_2$ (1)

For glycopeptide solid phase synthesis, as a solid phase carrier, Rink Amide-PEGA resin (0.05 mmol/g, 500 mg, 25 μmol) was used. An amino acid extension reaction was performed in a DMF solution of Fmoc amino acid derivative (75 μmol), HBTU (75 μmol), HOBt (75 μmol) and DIEA (150 μmol) for 5 minutes under the condition of microwave irradiation (40 W, 2450 MHz, 50° C.). A sugar chain substitution amino acid extension reaction was performed for 20 minutes under the similar condition using 1.5 equivalents of Fmoc-Thr (Ac6 core1)-OH: N-α-Fmoc-O—[O-(2,3,4,6-tetra-O-acetyl-β-D-galactopyranosyl)-(1→3)]-4,6-di-O-acetyl-2-acetamido-2-deoxy-α-D-galactopyranosyl}-L-threonine. Acetylation of an unreacted amino group was carried out by treatment with an acetic anhydride/DIEA/DMF (4.75:2.25:93 v/v/v) solution of 13 mM HOBt at room temperature for 5 minutes. Subsequently, a Fmoc group was deprotected by treatment with 20% piperidine/DMF for 3 minutes under the condition of microwave irradiation (40 W, 2450 MHz, 50° C.). For synthesis of glycopeptide, these three steps (i) extension with various Fmoc amino acids, (ii) acetylation treatment, (iii) removal of Fmoc treatment were sequentially repeated. The resulting solid phase resin was treated with trifluoroacetic acid:water:TIS (93:5:2 v/v/v) for 1 hour. After the reaction solution was filtered, and the solvent was distilled off, ether was added to the resulting residue for precipitation to obtain a crude crystal. The crude product was purified by reverse phase high performance liquid chromatography, to obtain an acetyl-protected sugar. The resulting protected sugar was dissolved in methanol, and a 1N aqueous sodium hydroxide solution was added thereto to adjust the pH to 12.0-12.5, followed by treatment at room temperature for 1 hour. After 10% acetic acid was added to adjust a pH to around 7, the solvent was distilled off. The resulting residue was purified by reverse phase high performance liquid chromatography to obtain Compound 1 as a lyophilized powder.

Lyophilized powder (26 mg, yield 46%). MALDI-TOF MS: m/z calcd for $C_{94}H_{152}N_{27}O_{37}$ [M+H]$^+$ 2251.1. Found 2250.7. ESI-HRMS: m/z calcd for $C_{94}H_{149}N_{27}O_{37}$ [M−2H]$^{2−}$ 1124.0304. Found 1124.0325 [M−2H]$^{2−}$. Amino acid analysis: Ala(4) 3.9, Asp(1) 1.0, Arg(1) 1.0, Gly(2) 2.0, His(1) 1.1, Pro(5) 5.4, Ser(2) 1.7, Thr(3) 2.8, Val(1) 1.0.

Synthesis of Example Compound 2

H-His-Gly-Val-Thr-Ser-Ala-Pro-Asp-<u>Thr</u>(Neu5Acα2→

3Galβ1→3GalNAcα)-Arg-Pro-Ala-Pro-Gly-Ser-Thr-Ala-

Pro-Pro-Ala-NH$_2$ (2)

A reaction was performed by allowing a solution of Compound 1 (22.5 mg), CMP-NANA (32.9 mg) and α2,3-(O)-sialic acid glycosyltransferase (44 mU) to stand at 25° C. for 24 hours under the condition of a 50 mM HEPES buffer (10 mM MnCl$_2$, 0.1% BSA, pH 7.0) (5.0 ml). The reaction mixture was purified by reverse phase high performance liquid chromatography to obtain Compound 2 as a lyophilized powder.

Lyophilized powder (20 mg, yield 80%). MALDI-TOF MS: m/z calcd for $C_{94}H_{152}N_{27}O_{37}$ [M+H]$^+$ 2251.1. Found 2250.7. ESI-HRMS: m/z calcd for $C_{94}H_{149}N_{27}O_{37}$[M−2H]$^{2−}$ 1124.0304. Found 1124.0325 [M−2H]$^{2−}$. Amino acid analysis: Ala(4) 3.9, Asp(1) 1.0, Arg(1) 1.0, Gly(2) 2.0, His(1) 1.1, Pro(5) 5.4, Ser(2) 1.7, Thr(3) 2.8, Val(1) 1.0.

Synthesis of Example Compound 3

H-His-Gly-Val-Thr-Ser-Ala-Pro-Asp-<u>Thr</u>(GalNAcα)-

Arg-Pro-Ala-Pro-Gly-Ser-Thr-Ala-Pro-Pro-Ala-

NH$_2$ (3)

As in Compound 1, Compound 3 was synthesized using Fmoc-Thr(Ac3Tn)-OH:N-α-Fmoc-O-(3,4,6-tri-O-acetyl-2-acetamido-2-deoxy-α-D-galactopyranosyl)-L-threonine.

Lyophilized powder (15 mg, yield 14%). MALDI-TOF MS: m/z calcd for $C_{88}H_{141}N_{27}O_{32}$[M+H]$^+$ 2089.0. Found 2089.1. ESI-HRMS: m/z calcd for $C_{88}H_{143}N_{27}O_{32}$[M+3H]$^{3+}$ 697.0157. Found 697.0174. Amino acid analysis: Ala(4) 4.0, Asp(1) 1.0, Arg(1) 1.0, Gly(2) 1.9, His(1) 1.0, Pro(5) 5.2, Ser(2) 1.7, Thr(3) 2.8, Val(1) 1.0.

Synthesis of Example Compound 4

H-His-Gly-Val-Thr-Ser-Ala-Pro-Asp-<u>Thr</u>(Neu5Acα2→

6GalNAcα)-Arg-Pro-Ala-Pro-Gly-Ser-Thr-Ala-Pro-

Pro-Ala-NH$_2$ (4)

As in Compound 1, Compound 4 was synthesized using Fmoc-Thr (Ac6 Sialyl Tn)-OH:N-α-Fmoc-O-{[methyl-(5- acetamido-4,7,8,9-tetra-O-acetyl-3,5-dideoxy-α-D-glycero-D-galacto-2-nonuropyranosyl)onato-(2→6)]-3,4-di-O-acetyl-2-acetamido-2-deoxy-α-D-galactopyranosyl}-L-threonine. After deacetylation of the sugar portion, the compound was dissolved in water, a 1N aqueous sodium hydroxide solution was added thereto to adjust a pH to 12.0 or lower, and treatment was performed at room temperature for 6 hours. After 10% acetic acid was added to adjust the pH to around 7, purification was performed to obtain Compound 4 as a lyophilized powder.

Lyophilized powder (2 mg, yield 15%). MALDI-TOF MS: m/z calcd for $C_{99}H_{158}N_{28}O_{40}$ [M+H]$^+$ 2380.1. Found 2380.1. ESI-HRMS: m/z calcd for $C_{99}H_{158}N_{28}O_{40}$ [M+3H]$^{3+}$ 794.0475. Found 794.0494. Amino acid analysis: Ala(4) 3.9, Asp(1) 1.0, Arg(1) 1.0, Gly(2) 1.9, His(1) 0.8, Pro(5) 5.1, Ser(2) 1.7, Thr(3) 2.8, Val(1) 1.0.

Synthesis of Example Compound 5

H-His-Gly-Val-Thr-Ser-Ala-Pro-Asp-<u>Thr</u>(Galβ1→3

[GlcNAcβ1→6]GalNAcα)-Arg-Pro-Ala-Pro-Gly-Ser-Thr-

Ala-Pro-Pro-Ala-NH₂ (5)

As in Compound 1, Compound 5 was obtained using Fmoc-Thr (Ac7 core2-OH:N-α-Fmoc-O-{(2,3,4,6-tetra-O-acetyl-β-D-galactopyranosyl)-(1→3)-O-[2-acetamido-3,4,6-tri-O-acetyl-2-deoxy-β-D-glucopyranosyl(1→6)]-2-acetamido-2-deoxy-α-D-galactopyranosyl}-L-threonine.

Lyophilized powder (51 mg, yield: 52%). MALDI-TOF MS: m/z calcd for $C_{102}H_{165}N_{28}O_{42}$[M+H]$^+$ 2454.2. Found 2454.5. ESI-HRMS: m/z calcd for $C_{102}H_{163}N_{28}O_{42}$[M−H]$^-$ 2452.1479. Found 2452.1475. Amino acid analysis: Ala(4) 3.7, Asp(1) 1.0, Arg(1) 1.0, Gly(2) 1.9, His(1) 0.9, Pro(5) 5.2, Ser(2) 1.6, Thr(3) 2.6, Val(1) 0.9.

Synthesis of Example Compound 6

H-His-Gly-Val-Thr-Ser-Ala-Pro-Asp-<u>Thr</u>(Neu5Acα2→

3Galβ1→3[GlcNAcβ1→6]GalNAcα)-Arg-Pro-Ala-Pro-Gly-

Ser-Thr-Ala-Pro-Pro-Ala-NH₂ (6)

A reaction was performed using a 50 mM HEPES buffer solution (10 mM MnCl₂, 0.1% BSA, pH 7.0) of Compound 5, CMP-NANA and α2,3-(O)-sialic acid transferase (5 mU/ml) to obtain Compound 6.

Lyophilized powder (6 mg, quant.). MALDI-TOF MS: m/z calcd for $C_{113}H_{182}N_{29}O_{50}$: [M+H]$^+$ 2745.3. Found 2745.8. ESI-HRMS: m/z calcd for $C_{113}H_{180}N_{29}O_{50}$ [M−H]$^-$ 2743.2434. Found 2743.2410.

Synthesis of Example Compound 7

H-His-Gly-Val-Thr-Ser-Ala-Pro-Asp-<u>Thr</u>(Neu5Acα2→

3Galβ1→3[Galβ1→4GlcNAcβ1α→6]GalNAcα)-Arg-Pro-Ala-

Pro-Gly-Ser-Thr-Ala-Pro-Pro-Ala-NH₂ (7)

A reaction was performed using a 50 mM HEPES buffer solution (10 mM MnCl₂, 0.1% BSA, pH 7.0) of Compound 5, UDP-Gal, CMP-NANA, β1,4-galactose transferase (100 mU/ml) and α2,3-(O)-sialic acid transferase (5 mU/ml) to obtain Compound 7.

Lyophilized powder (7 mg, quant.). MALDI-TOF MS: m/z calcd for $C_{119}H_{192}N_{29}O_{55}$ [M+H]$^+$ 2907.3. Found 2906.5. ESI-HRMS: m/z calcd for $C_{119}H_{190}N_{29}O_{55}$ [M−H]$^-$ 2905.2962. Found 2905.2922.

Synthesis of Example Compound 8

H-His-Gly-Val-Thr-Ser-Ala-Pro-Asp-<u>Thr</u>(Neu5Acα2→

3Galβ1→3[Neu5Acα2→3Galβ1→4GlcNAcβ1→6]GalNAcα)-

Arg-Pro-Ala-Pro-Gly-Ser-Thr-Ala-Pro-Pro-Ala-

NH₂ (8)

A reaction was performed using a 50 mM HEPES buffer (10 mM MnCl₂, 0.1% BSA, pH 7.0) solution of Compound 5, UDP-Gal, CMP-NANA, β1,4-galactose transferase (100 mU/ml), α2,3-(O)-sialic acid transferase (5 mU/ml) and α2,3-(N)-sialic acid transferase (74 mU/ml) to obtain Compound 8.

Lyophilized powder (7 mg, yield 46%). MALDI-TOF MS: m/z calcd for $C_{130}H_{209}N_{30}O_{63}$ [M+H]$^+$ 3198.4. Found 3198.0. ESI-HRMS: m/z calcd for $C_{130}H_{207}N_{30}O_{63}$ [M−H]$^-$ 3196.3916. Found 3196.3899.

Synthesis of Example Compound 9

H-His-Gly-Val-Thr-Ser-Ala-Pro-Asp-<u>Thr</u>(GlcNAcβ1→

6GalNAcα)-Arg-Pro-Ala-Pro-Gly-Ser-Thr-Ala-Pro-

Pro-Ala-NH₂ (9)

Under the same conditions as that of Compound 4, Compound 9 was synthesized using Fmoc-Thr (Ac5 core6)-OH: N-α-Fmoc-O-{[3,4,6-tri-O-acetyl-2-acetamido-2-deoxy-β-D-glucopyranosyl-(1→6)]-3,4-di-O-acetyl-2-acetamido-2-deoxy-α-D-galactopyranosyl}-L-threonine.

Lyophilized powder (17 mg, yield 30%). MALDI-TOF MS: m/z calcd for $C_{96}H_{155}N_{28}O_{37}$ [M+H]$^+$ 2292.1. Found 2290.6. ESI-HRMS: m/z calcd for $C_{96}H_{154}N_{28}O_{37}$[M+2H]$^{2+}$ 1146.5593. Found 1146.5568. Amino acid analysis: Ala(4) 4.1, Asp(1) 1.0, Arg(1) 1.0, Gly(2) 2.0, His(1) 1.0, Pro(5) 5.4, Ser(2) 1.7, Thr(3) 2.8, Val(1) 1.0.

Synthesis of Example Compound 10

H-His-Gly-Val-Thr-Ser-Ala-Pro-Asp-<u>Thr</u>(Galβ1→3

[Neu5Acα2→6]GalNAcα)-Arg-Pro-Ala-Pro-Gly-Ser-Thr-

Ala-Pro-Pro-Ala-NH₂ (10)

As in Compound 1, Compound 10 was obtained using Fmoc-Thr (Ac6 2,6-Sialyl T)-OH:N-α-Fmoc-O-{[(2,3,4,6-tetra-O-acetyl-β-D-galactopyranosyl)-(1→3)]-O-[methyl-(5-acetamido-4,7,8,9-tetra-O-acetyl-3,5-dideoxy-α-D-glycero-D-galacto-2-nonuropyranosyl)onato-(2→6)]-2-acetamido-2-deoxy-α-D-galactopyranosyl}-L-threonine.

Lyophilized powder (6 mg, yield 390). MALDI-TOF MS: m/z calcd for $C_{105}H_{169}N_{28}O_{45}$ [M+H]$^+$ 2542.2. Found 2452.6. ESI-HRMS: m/z calcd for $C_{105}H_{170}N_{28}O_{45}[M+2H]^{2+}$ 1271.5937. Found 1271.5945. Amino acid analysis: Ala(4) 3.8, Asp(1) 1.0, Arg(1) 1.0, Gly(2) 1.9, His(1) 0.9, Pro(5) 5.2, Ser(2) 1.6, Thr(3) 2.7, Val(1) 0.9.

Synthesis of Example Compound 11

H-His-Gly-Val-Thr-Ser-Ala-Pro-Asp-<u>Thr</u>(Neu5Acα2→

3Galβ1→3[Neu5Acα2→6]GalNAcα)-Arg-Pro-Ala-Pro-Gly-

Ser-Thr-Ala-Pro-Pro-Ala-NH$_2$ (11)

Compound 11 was synthesized under the same conditions as that of Compound 2.
Lyophilized powder (2 mg, quant.). MALDI-TOF MS: m/z calcd for $C_{116}H_{186}N_{29}O_{53}$ [M+H]$^+$ 2833.3. Found 2833.2. ESI-HRMS: m/z calcd for $C_{116}H_{187}N_{29}O_{53}$ [M+2H]$^{2+}$ 1417.1415. Found 1417.1446. Amino acid analysis: Ala(4) 3.8, Asp(1) 1.0, Arg(1) 1.0, Gly(2) 1.9, His(1) 0.8, Pro(5) 5.2, Ser(2) 1.6, Thr(3) 2.7, Val(1) 0.9.

Synthesis of Example Compound 12

H-His-Gly-Val-<u>Thr</u>(Neu5Acα2→3Galβ1→3GalNAcα)-Ser-

Ala-Pro-Asp-Thr-Arg-Pro-Ala-Pro-Gly-Ser-Thr-Ala-

Pro-Pro-Ala-NH$_2$ (12)

Compound 12 was synthesized under the same conditions as that of Compound 2.
Lyophilized powder (2 mg, yield 14%). MALDI-TOF MS: m/z calcd for $C_{105}H_{169}N_{28}O_{45}$ [M+H]$^+$ 2542.2. Found 2451.6. ESI-HRMS: m/z calcd for $C_{105}H_{168}N_{28}O_{45}$ [M+3H]$^{3+}$ 848.0651. Found 848.0668. Amino acid analysis: Ala(4) 4.0, Asp(1) 1.0, Arg(1) 1.0, Gly(2) 2.0, His(1) 0.8, Pro(5) 5.3, Ser(2) 1.7, Thr(3) 2.8, Val(1) 1.0.

Synthesis of Example Compound 13

H-His-Gly-Val-Thr-Ser-Ala-Pro-Asp-Thr-Arg-Pro-

Ala-Pro-Gly-Ser-Thr-Ala-Pro-Pro-Ala-His-Gly-Val-

Thr-Ser-Ala-Pro-Asp-Thr-Arg-Pro-Ala-Pro-Gly-Ser-

Thr-Ala-Pro-Pro-Ala-NH$_2$ (13)

Compound 13 was synthesized under the same conditions as that of Compound 1.
Lyophilized powder (11 mg, yield 20%). MALDI-TOF MS: m/z calcd for $C_{160}H_{253}N_{51}O_{54}$ [M+H]$^+$ 3753.9. Found 3751.1 ESI-HRMS: m/z calcd for $C_{160}H_{253}N_{51}O_{54}$ [M+4H]$^{4+}$ 939.2233. Found 939.2245. Amino acid analysis: Ala(4) 4.1, Asp(1) 1.0, Arg(1) 1.0, Gly(2) 2.0, His(1) 0.9, Pro(5) 5.3, Ser(2) 1.7, Thr(3) 2.8, Val(1) 0.9.

Synthesis of Example Compound 14

Biotin-PEG-linker-His-Gly-Val-Thr-Ser-Ala-Pro-

Asp-<u>Thr</u>(Neu5Acα2→6GalNAcα)-Arg-Pro-Ala-Pro-Gly-

Ser-Thr-Ala-Pro-Pro-Ala-NH2 (14)

Biotinylation glycopeptide solid phase synthesis was performed in accordance with synthesis which was similar to afore-mentioned synthesis. For a sugar chain substitution amino acid extension reaction, 1.5 equivalents of N-α-Fmoc-O-{methyl O-4',7',8',9'-tetra-O-acetyl-5'-N-acetamido-neuraminate-(2'→6)-3,4-di-O-acetyl-2-acetamido-2-deoxy-α-D-galactopyranosyl}-L-threonine was used, and at the final stage, 5 equivalents of PEG reagent, and biotin were condensed to synthesize Compound 14.
Lyophilized powder (2 mg, yield 7.4%), MALDI-TOF MS: m/z calcd for $C_{119}H_{191}N_{32}O_{46}S$ [M+H]$^+$ 2836.3. Found 2836.6.

Synthesis of Example Compound 15

Biotin-PEG-linker-[His-Gly-Val-Thr-Ser-Ala-Pro-

Asp-<u>Thr</u>(Neu5Acα2→6GalNAcα)-Arg-Pro-Ala-Pro-Gly-

Ser-Thr-Ala-Pro-Pro-Ala]$_2$-NH$_2$ (15)
[40 mer glycopeptide]

Compound 15 was synthesized under the same conditions as that of Compound 12.
Lyophilized powder (2.0 mg, yield 7.7%), MALDI-TOF MS: m/z calcd for $C_{218}H_{346}N_{59}O_{86}S$ [M+H]$^+$ 5198.4. Found 5206.5

Synthesis of Example Compound 16

Biotin-PEG-linker-[His-Gly-Val-Thr-Ser-Ala-Pro-

Asp-<u>Thr</u>(Neu5Acα2→6GalNAcα)-Arg-Pro-Ala-Pro-Gly-

Ser-Thr-Ala-Pro-Pro-Ala]$_3$-NH$_2$ (16)
[60 mer glycopeptide]

Compound 16 was synthesized under the same conditions as that of Compound 12.
Lyophilized powder (1.8 mg, yield 4.7%), MALDI-TOF MS: m/z calcd for $C_{317}H_{501}N_{86}O_{126}S$ [M+H]$^+$ 7560.5. Found 7576.3.

Synthesis of Example Compound 17

Biotin-PEG-linker-[His-Gly-Val-Thr-Ser-Ala-Pro-

Asp-<u>Thr</u>(Neu5Acα2→6GalNAcα)-Arg-Pro-Ala-Pro-Gly-

Ser-Thr-Ala-Pro-Pro-Ala]$_4$-NH$_2$ (17)
[80 mer glycopeptide]

Compound 17 was synthesized under the same conditions as that of Compound 12.
Lyophilized powder (1.1 mg, yield 2.3%), MALDI-TOF MS: m/z calcd for $C_{416}H_{656}N_{113}O_{166}S$ [M+H]$^+$ 9922.6. Found 9930.8.

Synthesis of Example Compound 18

Biotin-PEG-linker-[His-Gly-Val-Thr-Ser-Ala-Pro-

Asp-<u>Thr</u>(Neu5Acα2→6GalNAcα)-Arg-Pro-Ala-Pro-Gly-

Ser-Thr-Ala-Pro-Pro-Ala]$_5$-NH$_2$ (18)
[100 mer glycopeptide]

Compound 18 was synthesized under the same conditions as that of Compound 12.

Lyophilized powder (1.7 mg, yield 2.7%), MALDI-TOF MS: m/z calcd for $C_{515}H_{811}N_{140}O_{206}S$ [M+H]$^+$ 12284.7. Found 12201.9.

Synthesis of Example Compound 19

A reaction was performed for 20 minutes using 1.5 equivalents of Fmoc-Thr(O-Me Ac6 Sialyl Tn)-OH:N-α-Fmoc-O-{methyl O-4',7',8',9'-tetra-O-acetyl-5'-N-acetamido-neuraminate-(2'→6)-3,4-di-O-acetyl-2-acetamido-2-deoxy-α-D-galactopyranosyl}-L-threonine, under the same conditions. Acetylation of an unreacted amino group was carried out by treatment with an acetic anhydride/DIEA/DMF (4.75:2.25:93 v/v/v) solution of 13 mM HOBt at a room temperature for 5 minutes. Subsequently, a Fmoc group was deprotected by treatment with 20% piperidine/DMF for 3 minutes under the condition of microwave irradiation (40 W, 2450 MHz, 50° C.). For synthesis of glycopeptide, these three steps (i) extension with various Fmoc amino acids, (ii) acetylation treatment, (iii) removal of Fmoc treatment were sequentially repeated. The resulting solid phase resin was treated with trifluoroacetic acid:water:TIS (93:5:2 v/v/v) for 1 hour. After the reaction solution was filtered, and the solvent was distilled off, ether was added to the resulting residue for precipitation to obtain a crude crystal. The crude product was purified by reverse phase high performance liquid chromatography, to obtain an acetyl-protected sugar. The resulting protected sugar was dissolved in methanol, and a 1N aqueous sodium hydroxide solution was added thereto to adjust the pH to 12.0-12.5, followed by treatment at room temperature for 1 hour. After 10% acetic acid was added to adjust a pH to around 7, the solvent was distilled off. Next, the resulting methyl ester was dissolved in water, a 1N aqueous sodium hydroxide solution was added thereto to adjust a pH to 10.5-11.0, and treatment was performed at room temperature for 1 hour. The resulting residue was purified by reverse phase high performance liquid chromatography to obtain Compound 19 as a lyophilized powder.

Lyophilized powder (17 mg, yield 22%). MALDI-TOF MS: m/z calcd for $C_{102}H_{164}N_{29}O_{41}S$ [M+H]$^+$ 2483.1. Found 2482.2.1.

Hereinafter, chemical formulas of the Example Compounds will be shown.

[Chemical Formula 1]
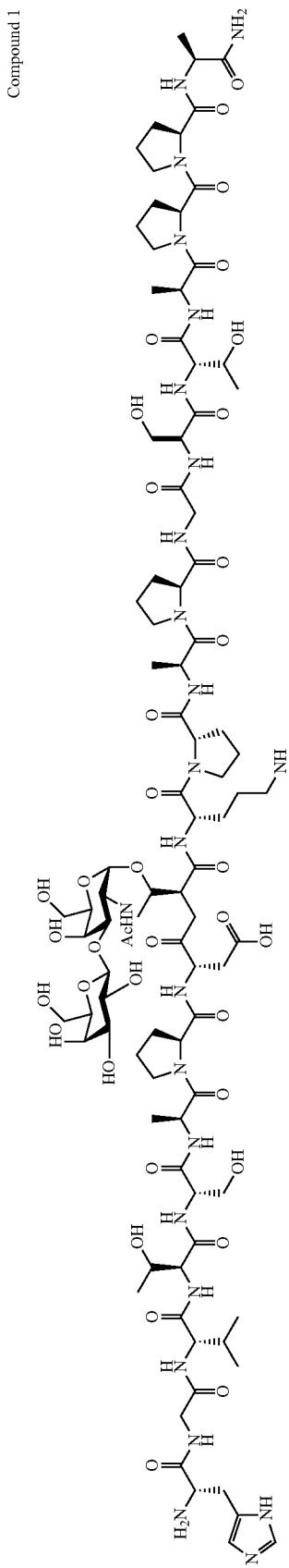
Compound 1
[Chemical Formula 2]
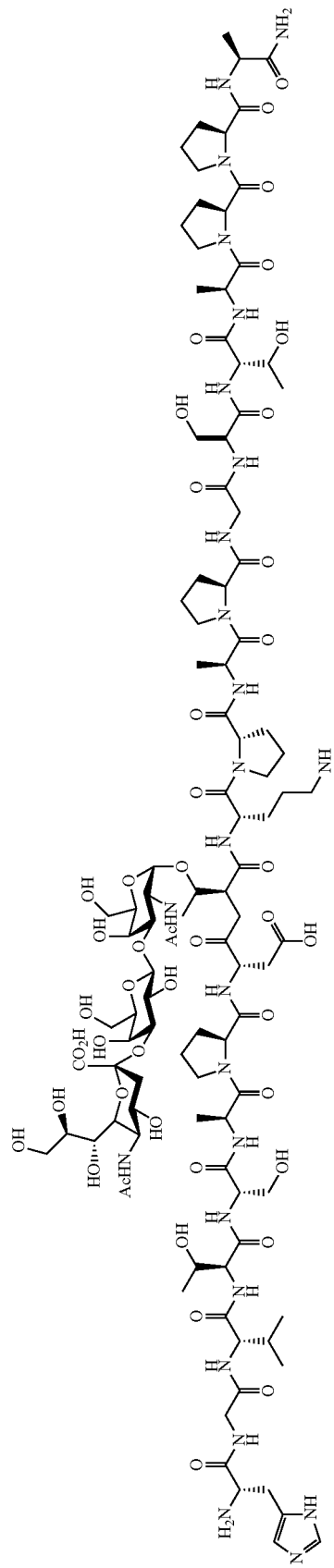
Compound 2

-continued
[Chemical Formula 3]
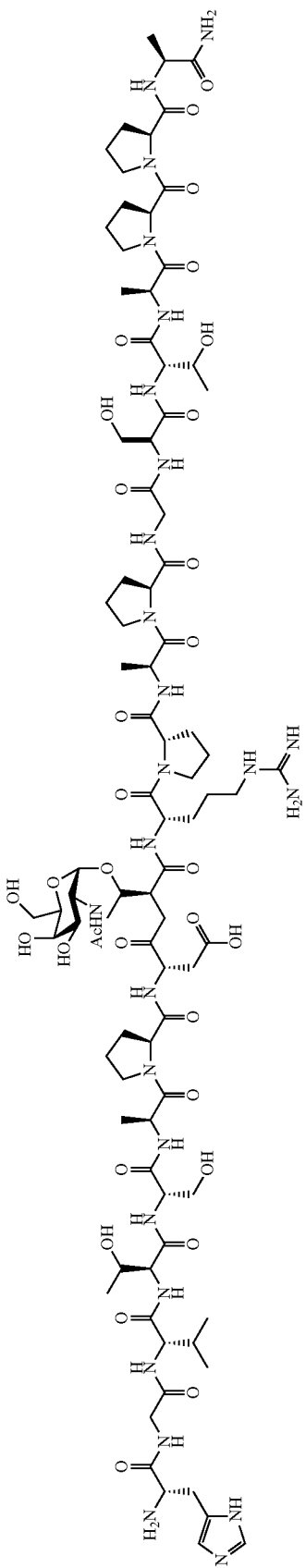
Compound 3
[Chemical Formula 4]
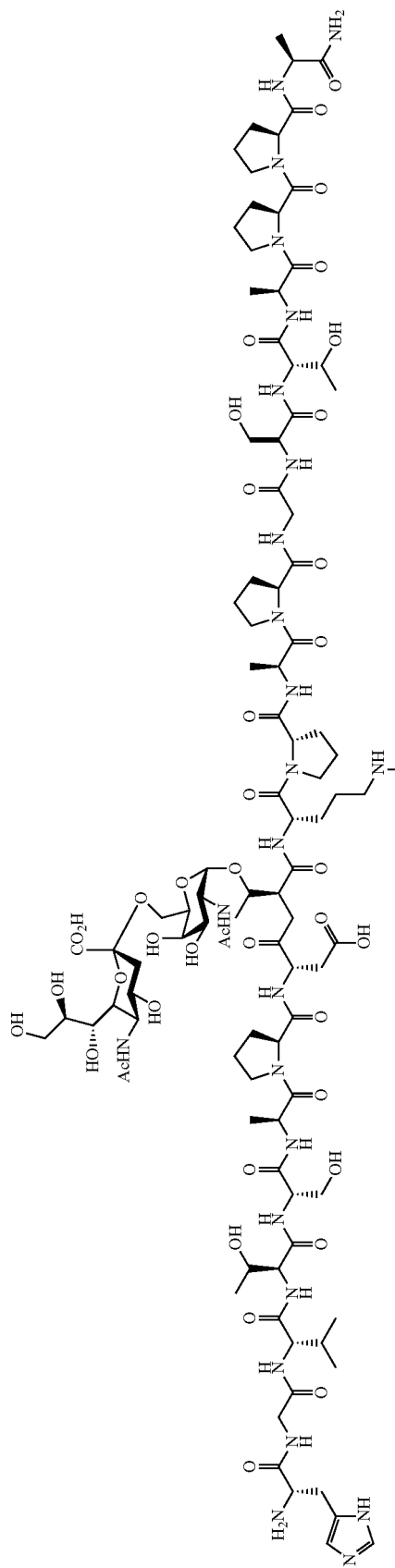
Compound 4

-continued
[Chemical Formula 5]
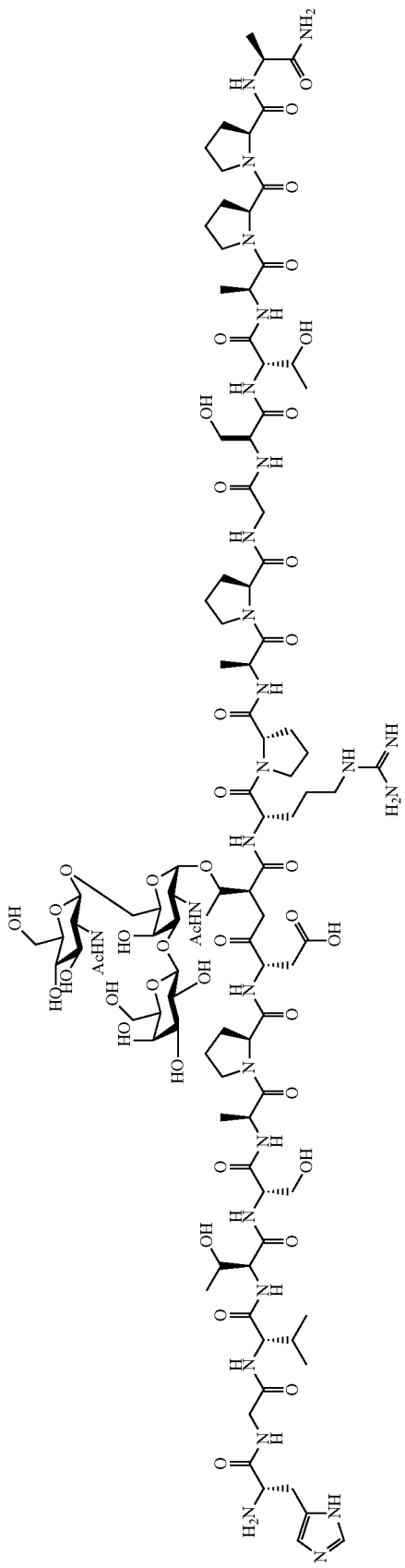
Compound 5
[Chemical Formula 6]
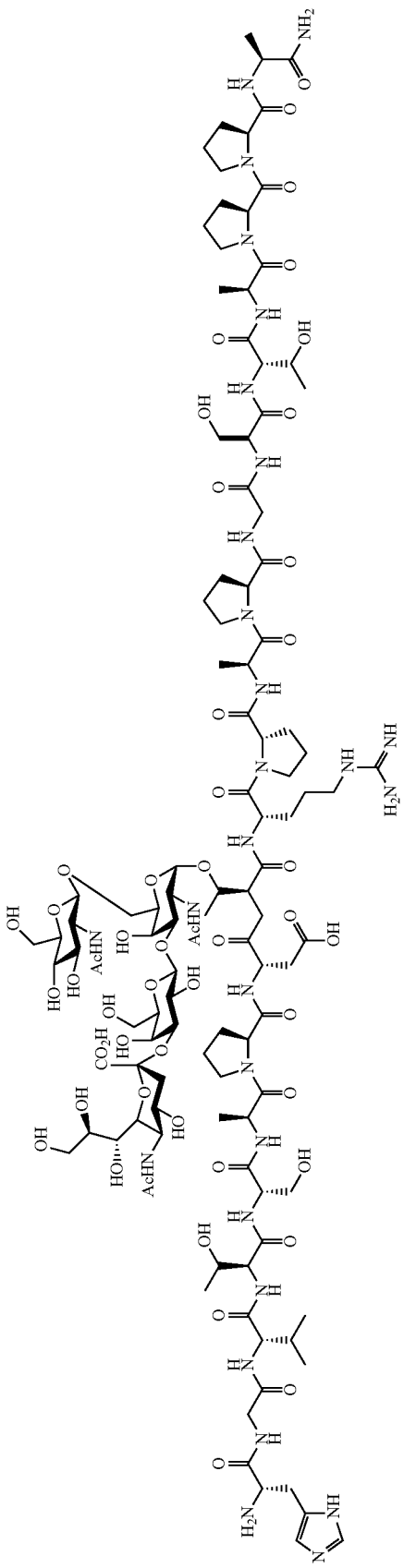
Compound 6

[Chemical Formula 7]
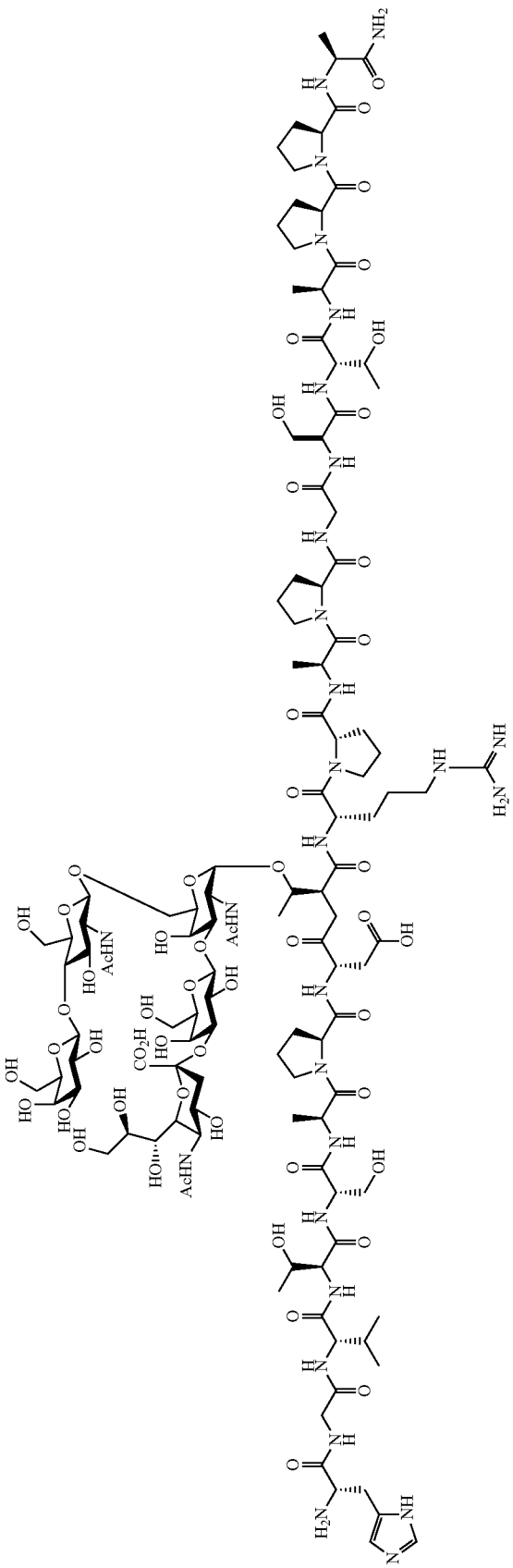
Compound 7

[Chemical Formula 8]
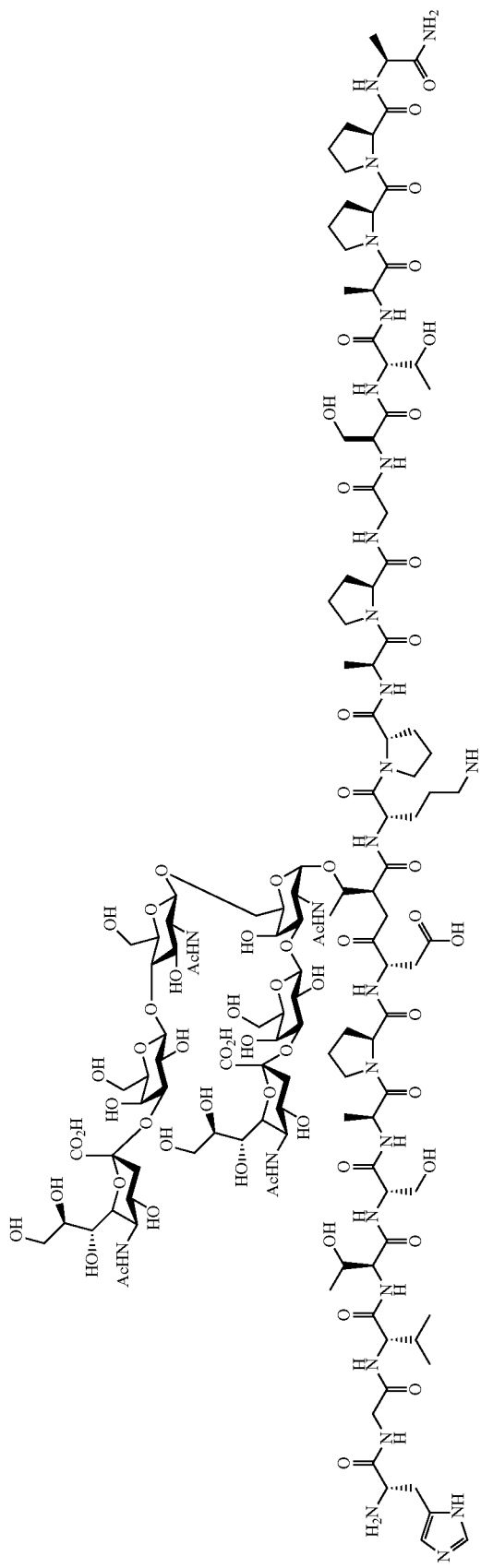
Compound 8
[Chemical Formula 9]
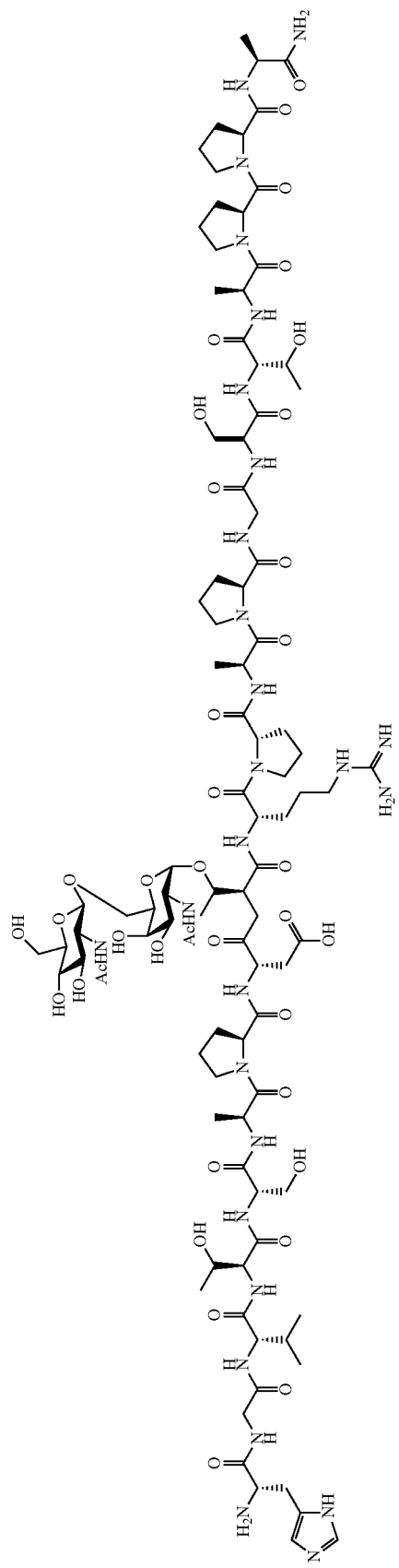
Compound 9

-continued
[Chemical Formula 10]
Compound 10
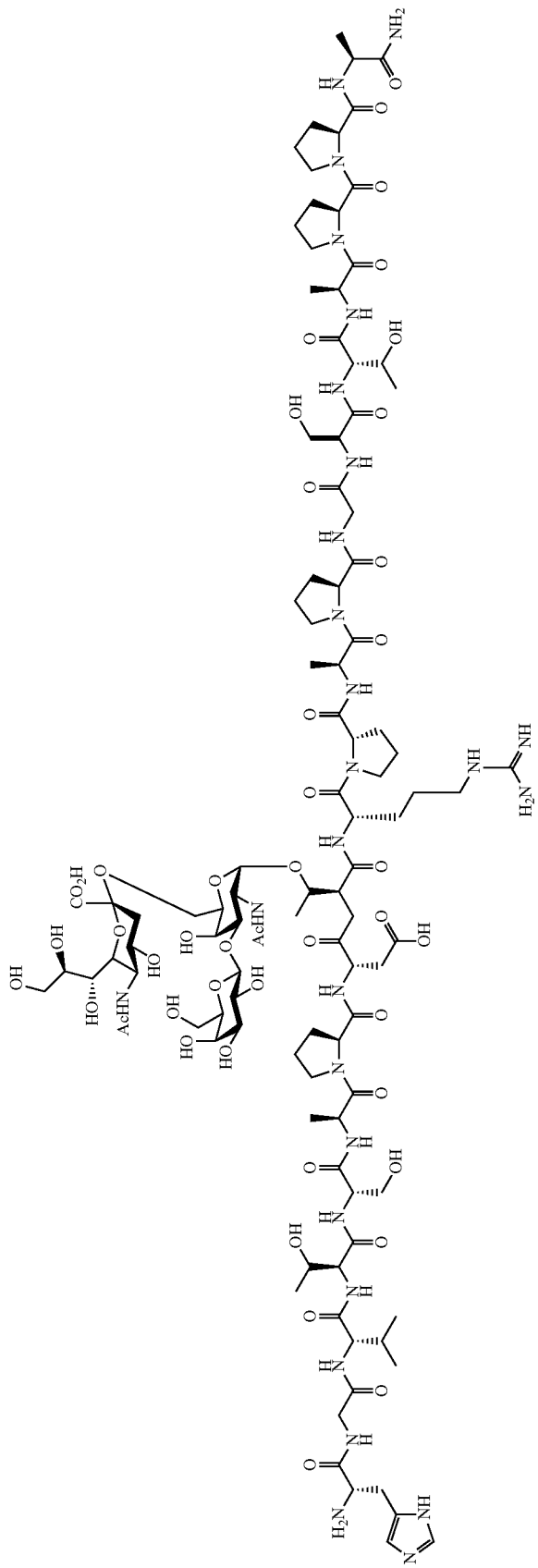

-continued
[Chemical Formula 11]
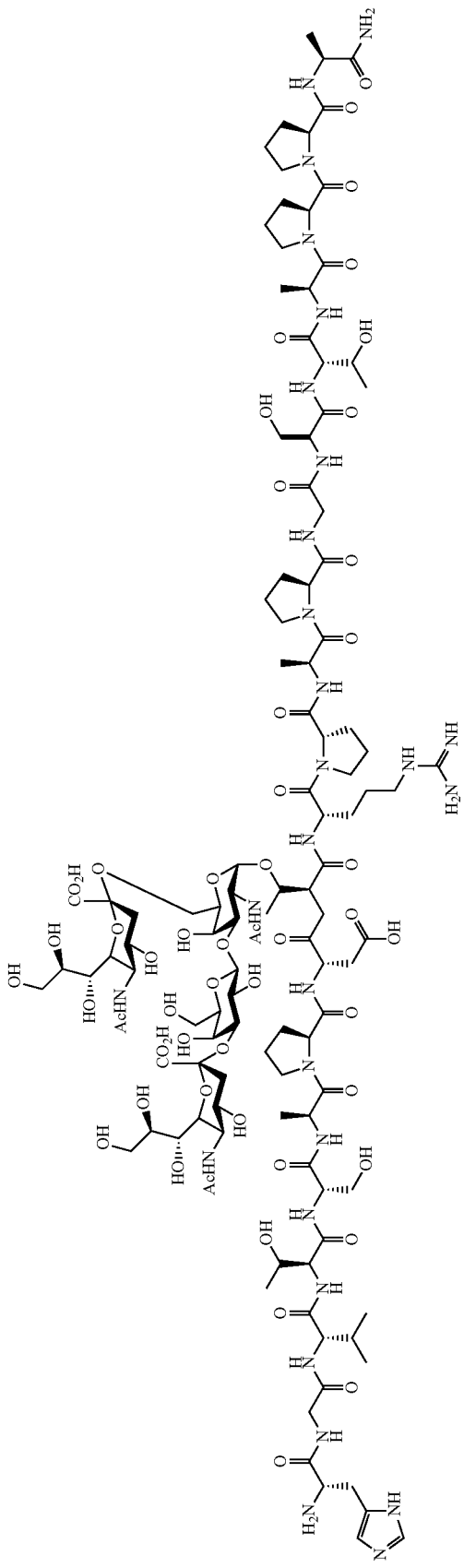
Compound 11
[Chemical Formula 12]
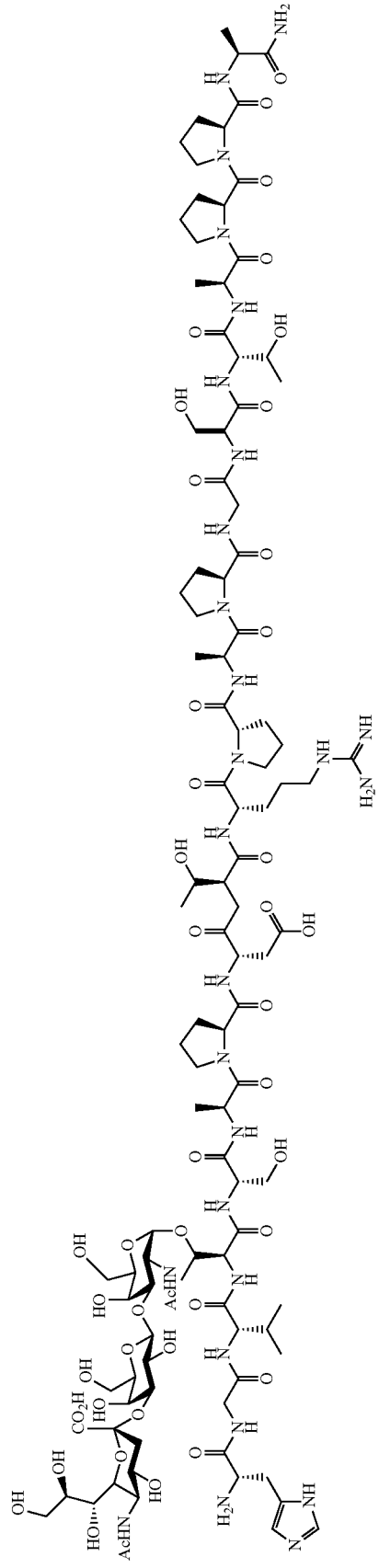
Compound 12

[Chemical Formula 13]
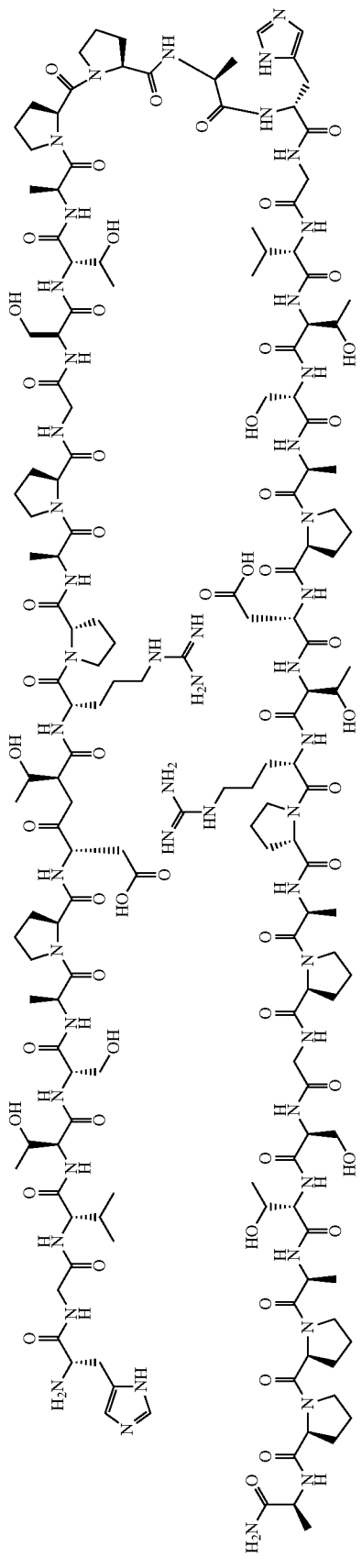
Compound 13
[Chemical Formula 14]
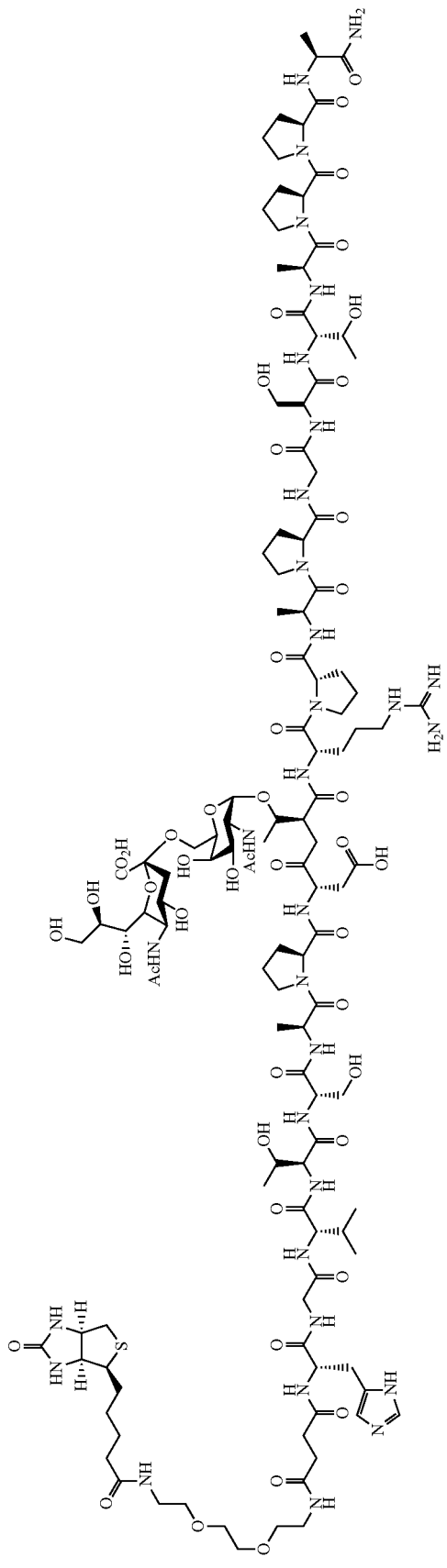
Compound 14

-continued
Compound 15
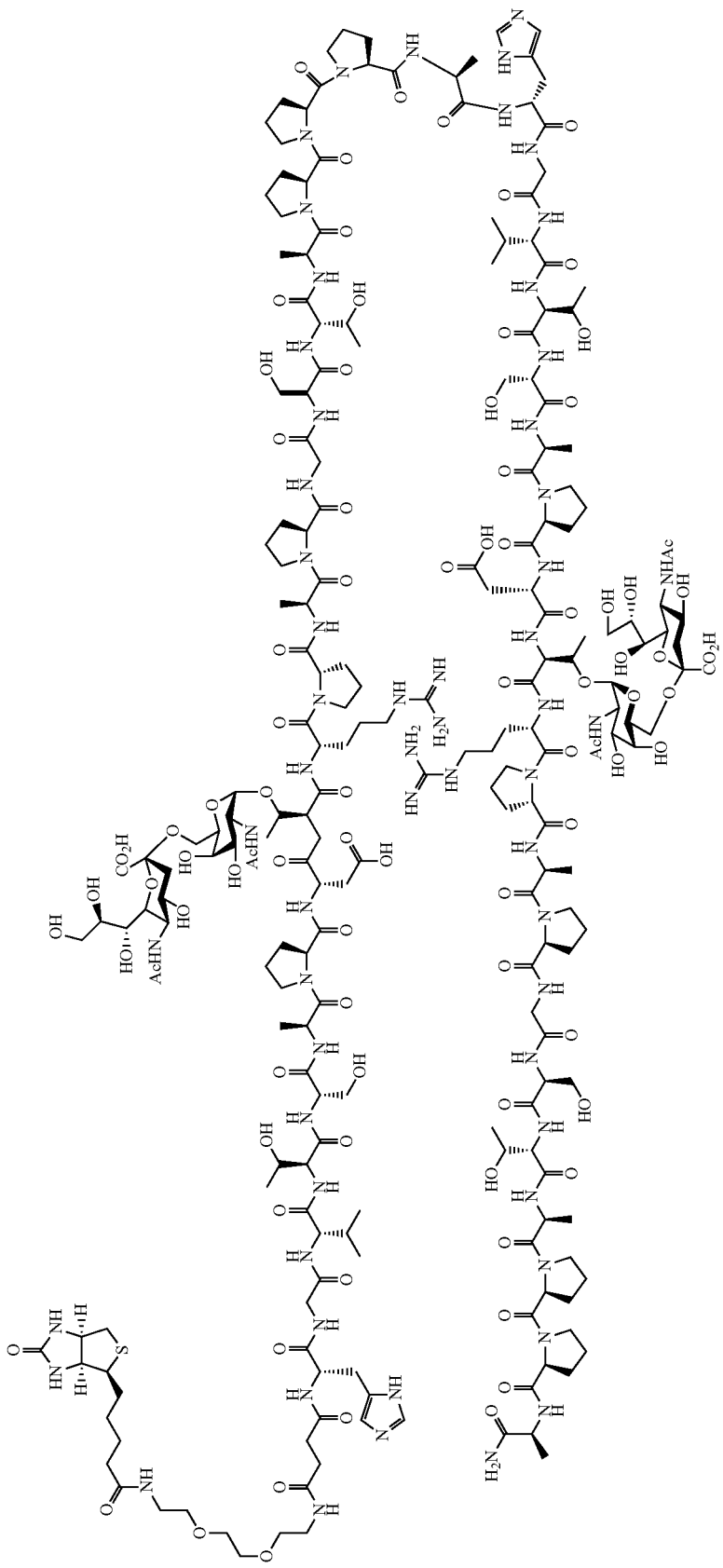
[Chemical Formula 15]

[Chemical Formula 16]
Compound 16
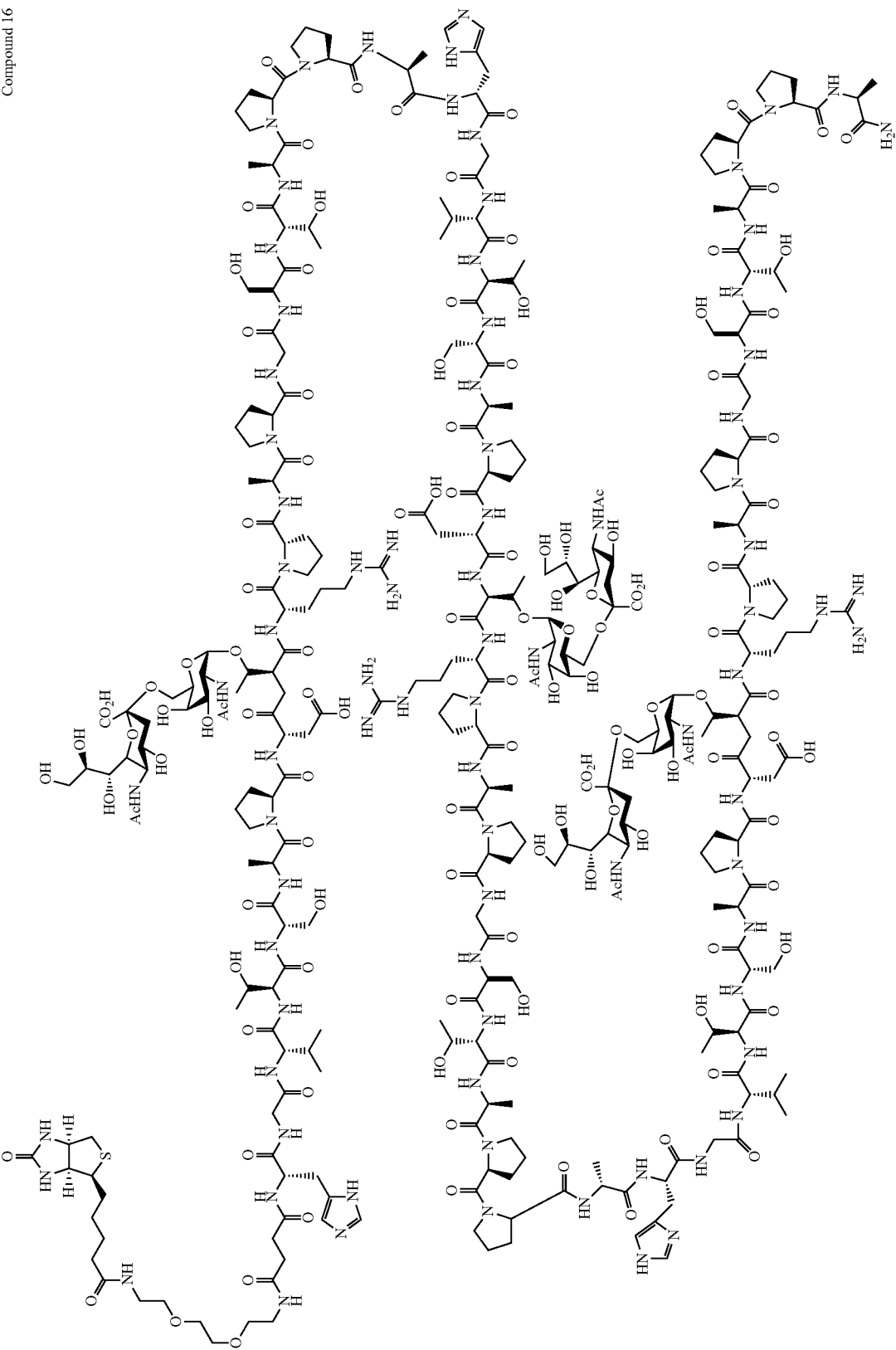

-continued
Compound 17
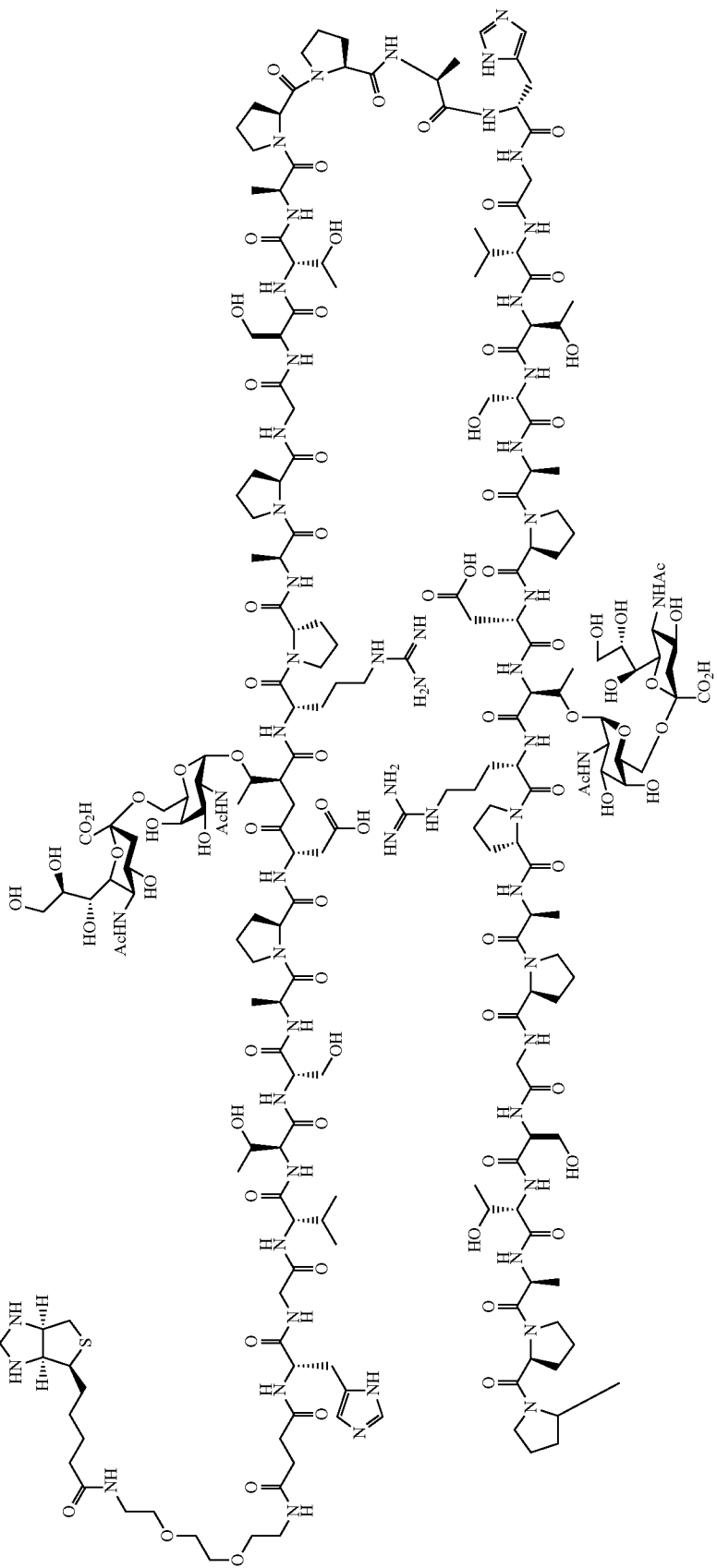
[Chemical Formula 17]

-continued
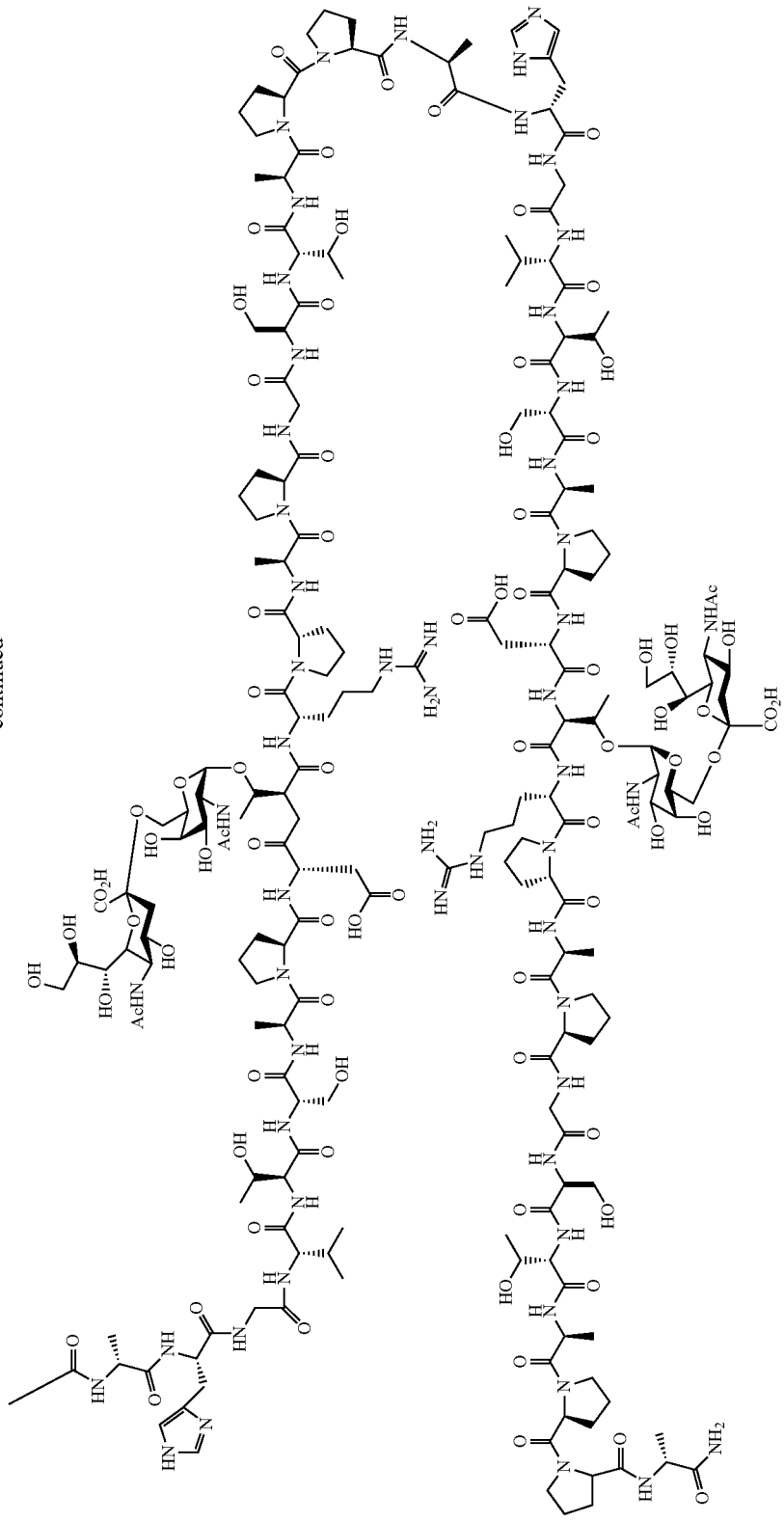

Compound 18
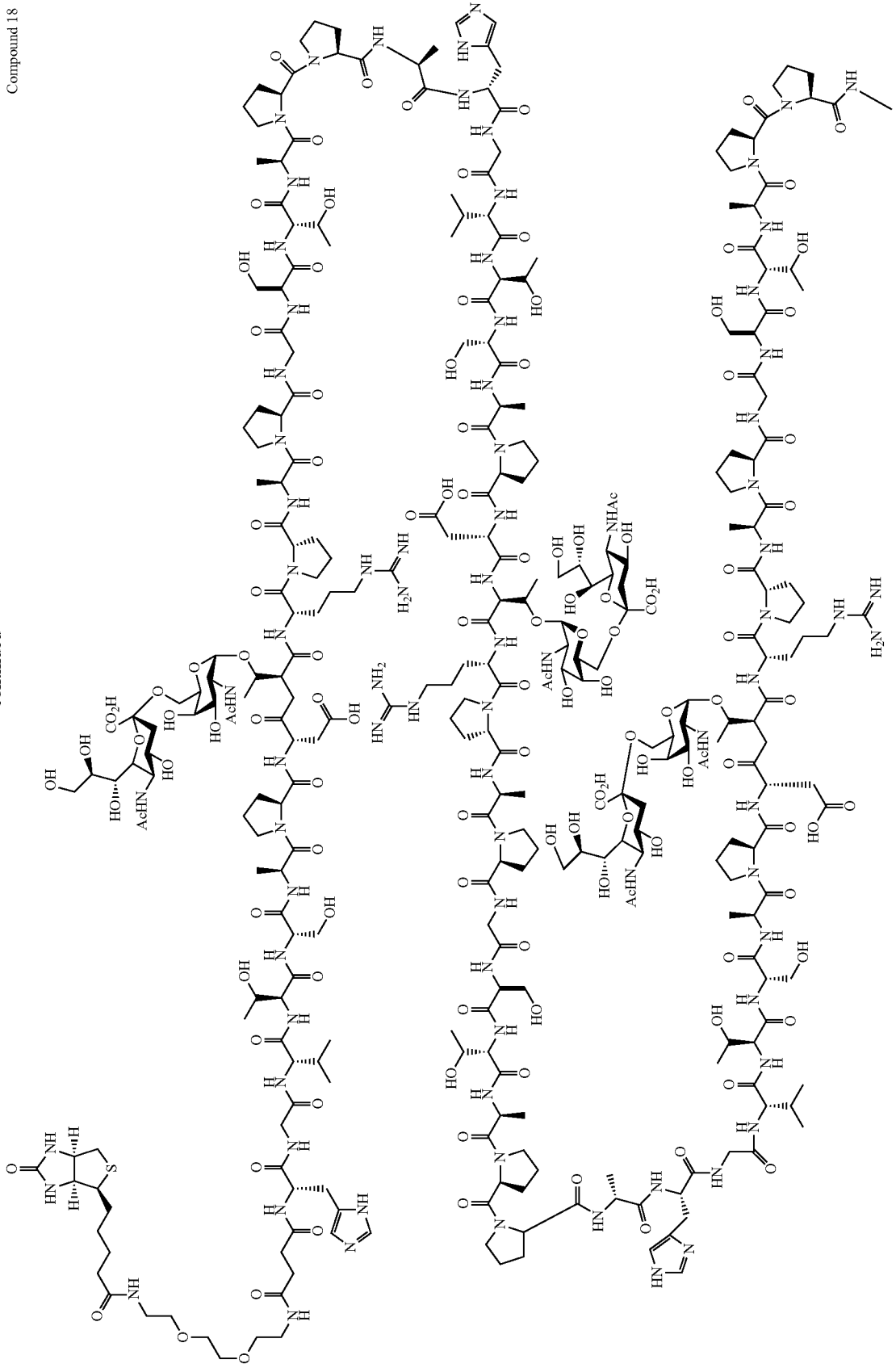

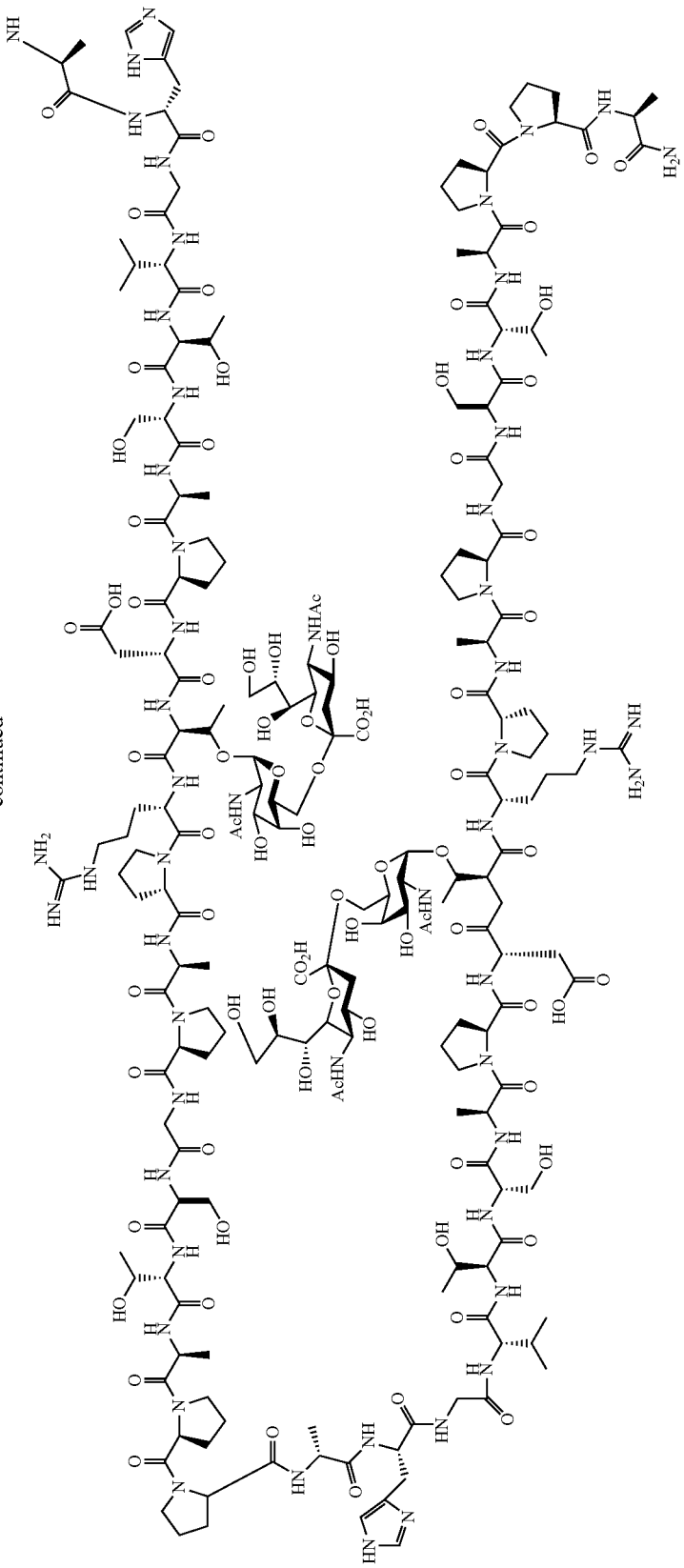

[Chemical Formula 19]
Compound 19
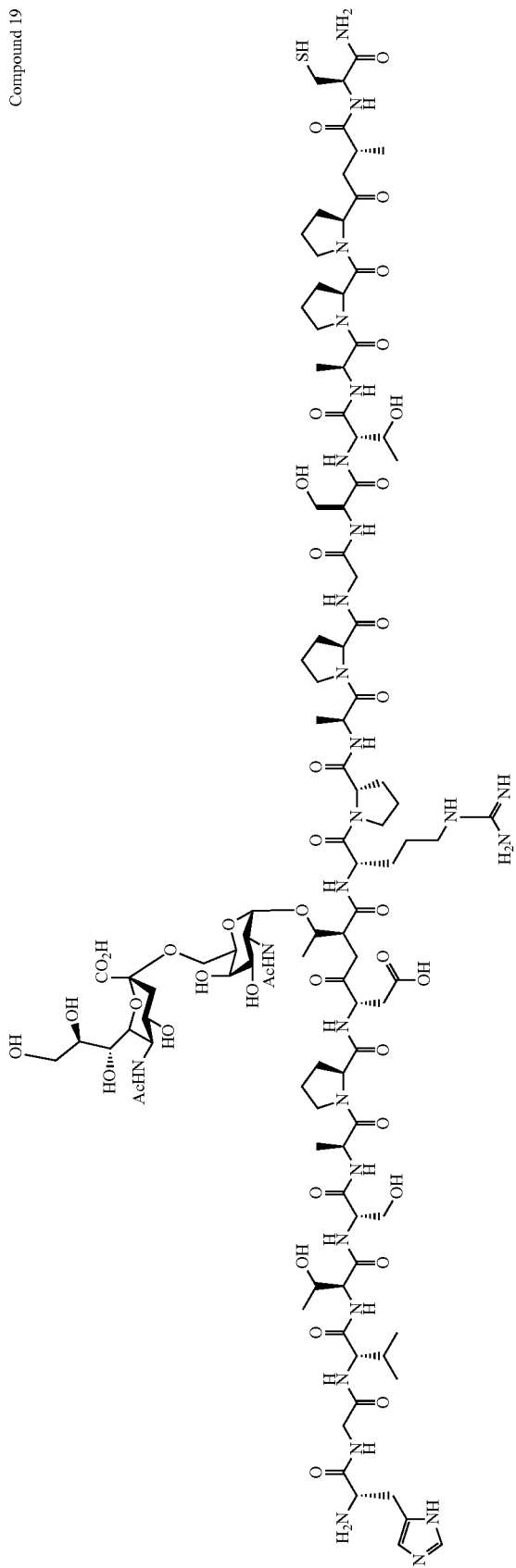

Compound Nos. 1 to 19 were named as in Table 1.

TABLE 1

| Compound Nos. | Name |
| --- | --- |
| 1 | T(DT*R)-20 |
| 2 | 2,3-ST(DT*R)-20 |
| 3 | Tn(DT*R)-20 |
| 4 | STn(DT*R)-20 |
| 5 | T6G(DT*R)-20 |
| 6 | 2,3ST6G(DT*R)-20 |
| 7 | 2,3ST6L(DT*R)-20 |
| 8 | 2,3ST6SL(DT*R)-20 |
| 9 | C6(DT*R)-20 |
| 10 | ST2-6(DT*R)-20 |
| 11 | dST(DT*R)-20 |
| 12 | 2,3ST(VT*S)-20 |
| 13 | 40 |
| 14 | Biotin-STn(DT*R)-20 |
| 15 | Biotin-STn(DT*R)-40 |
| 16 | Biotin-STn(DT*R)-60 |
| 17 | Biotin-STn(DT*R)-80 |
| 18 | Biotin-STn(DT*R)-100 |
| 19 | STn(DT*R)-20-Cys |

Example 2

Production of MUC1-Specific Antibody (Preparation of Immunogen)

4.18 mg of STn(DT*R)-20-Cys was dissolved in 0.1 M phosphate buffer containing 5 mM EDTA, 1 ml of aqueous solution containing 10 mg Imject Maleimide activated mariculture keyhole limpet hemocyanin (manufactured by Thermo scientific) was added thereto, and a reaction was allowed to progress at room temperature for 2 hours, and further the reaction was allowed to progress at 4° C. overnight. Dialysis of the reaction solution to purified water was performed and then lyophilization was performed to obtain immunogen.

100 μg of the prepared immunogen was administered intraperitoneally to a 4-week old Balb/c female mouse together with a Freund's complete adjuvant, as an initial immunization. After 21 days and after 42 days, 100 μg of an immunogen was administered with a Freund's incomplete adjuvant, as additional immunizations. Further, after 71 days, a solution obtained by suspending 100 μg of an immunogen in 0.1 ml of physiological saline was intraperitoneally administered, as a final immunization.

(Production of Hybridoma)

Three days after final immunization, the spleen was isolated, and spleen cells were recovered. The spleen cells and mouse myeloma cells (p3×63-Ag8. U1, Tokyo Tumor Mass Laboratory) were fused using 50% polyethylene glycol 4000, and a hybridoma was selected on a medium containing hypoxanthine, aminopterin and thymidine.

(Selection of MUC1 Antibody)

Ten days after cell fusion, screening of a specific antibody-producing cell was performed. ELISA used in screening was as follows. To each well of a 384-well microtiter plate (manufactured by Nunc), 35 μl of a Tris buffer (50 mM Tris-HCl, pH 7.5) containing 0.35 μg of an anti-mouse IgG antibody (manufactured by Shibayagi Co., Ltd.) was added to immobilize the antibody at 4° C. for 16 hours. After these wells were washed with 90 μl of a washing solution (physiological saline containing 0.01% Tween 20) once, 200 μl of BLOCK ACE (manufactured by Dainippon Sumitomo Pharma Co., Ltd.) was added, and this was allowed to stand at room temperature for 2 hours for blocking (an anti-mouse IgG antibody solid-phased plate). After each well was washed with 90 μl of a washing solution once, 10 μl of a hybridoma culture supernatant, 10 μl of a buffer A (50 mM Tris buffer containing 0.5% bovine serum albumin, 0.01% Tween 80, 0.05% Proclin 150, and 0.15 M NaCl, pH 7.4), and 10 μl of a buffer A containing 0.01 ng of Biotin-STn(DT*R)-20-Cys and 2 ng of Streptavidin-HRP (manufactured by PIERCE) were added to perform a reaction at 4° C. for 16 hours. Then, after each well was washed with 90 μl of a washing solution three times, 25 μl of TMB+Substrate-Chromogen (manufactured by DAKO) was added to develop a color at room temperature for 30 minutes, 25 μl of 0.05 M sulfuric acid was added to stop the reaction, and absorbance was measured at 450 nm.

From the result of screening, a clone (12D10) exhibiting strong affinity for STn(DT*R)-20 was obtained. Using a mouse monoclonal antibody isotyping ELISA kit (manufactured by BD Bioscience), a subclass of the antibody was determined and, as a result, an isotype of 12D10 was IgG2a. For this 12D10 antibody, the sequence of a variable region was determined using a common method. The result is shown in FIG. 4.

Example 3

Measurement of Antibody Specificity (Sugar Chain Specificity)

Fifteen (15) μl of a buffer A containing a MUC1 antibody was added to an anti-mouse IgG antibody solid-phased plate and the reaction was allowed to progress at room temperature for 3 hours. Then, after each well was washed with 90 μl of a washing solution three times, 15 μl of a buffer A containing Streptavidin-HRP, and Biotin-STn(DT*R)-20, and each of T(DT*R)-20, 2,3-ST(DT*R)-20, Tn(DT*R)-20, STn(DT*R)-20, 2,3ST6G(DT*R)-20, 2,3ST6L(DT*R)-20, 2,3-ST6SL (DT*R)-20, C6(DT*R)-20, ST2-6(DT*R)-20, dST(DT*R)-20, 2,3ST(VT*S)-20, 40, to perform a reaction at 4° C. for 16 hours. Then, after each well was washed with 90 μl of a washing solution three times, 15 μl of TMB+Substrate-Chromogen (manufactured by DAKO) was added to develop a color at room temperature for 30 minutes, 15 μl of 0.05 M sulfuric acid was added to stop the reaction, and absorbance at 450 nm was measured. As a result, it was shown that 12D10 exhibits high affinity for a sugar chain structure (STn(DT*R)-20, ST2-6(DT*R)-20, dST(DT*R)-20) highly expressed in cancer cells, but has low cross reactivity with a sugar chain structure (2,3ST6L(DT*R)-20, 2,3-ST6SL(DT*R)-20) highly expressed in normal cells (FIG. 1a, Table 2). From the foregoing, 12D10 was shown to have high specificity to sugar-chain type MUC1 highly expressed in cancer cells. On the other hand, it was shown that the other MUC1 antibodies, such as PankoMab (Cancer Immunol Immunother, 2006, Vol. 55, pp. 1337-1347, United States Patent Application Publication No. 2006/0292643), VU-2G7 (Tumor Biology Vol. 21, No. 4, pp. 197-210, 2000) and SM3, exhibit low affinity for a sugar chain structure (STn(DT*R)-20, ST2-6(DT*R)-20, dST(DT*R)-20) and have higher cross reactivity with a sugar chain structure (2,3ST6L(DT*R)-20, 2,3-ST6SL(DT*R)-20) highly expressed in normal cells, than 12D10 (FIGS. 1b, c, d and Table 2). From the foregoing, it was shown that 12D10 has higher specificity to MUC1 highly expressed in cancer cells, than PankoMab, VU-2G7 or SM3.

TABLE 2

| | | Cross reactivity [%] when cross reactivity with STn is 100% | | | |
|---|---|---|---|---|---|
| Compound No. | Glycopeptide | 12D10 | PankoMab | VU-2G7 | SM3 |
| 1 | T | 2.4 | 754 | 70 | 193 |
| 2 | 2,3-ST | 2.2 | 2002 | 67 | 145 |
| 3 | Tn | 1.4 | 498 | 179 | 186 |
| 4 | STn | 100 | 100 | 100 | 100 |
| 6 | 2,3ST6G | 1.6 | 29 | 324 | 223 |
| 7 | 2,3ST6L | 1.6 | 32 | 250 | 29 |
| 8 | 2,3ST6SL | 1.6 | 33 | 293 | 51 |
| 9 | C6 | 1.2 | 22 | 96 | 218 |
| 10 | ST2-6 | 90 | 89 | 226 | 77 |
| 11 | dST | 62 | 146 | 177 | 50 |
| 12 | 2,3ST(VT*S) | <0.10 | 22 | <5.6 | <10.3 |
| 13 | Non-glycosylated | 0.13 | 64 | <5.6 | 32 |

(Tandem Repeat Dependency)

To each well of a 384-well microtiter plate (manufactured by Nunc), 35 μl of a Tris buffer (50 mM Tris-HCl, pH 7.5) containing 0.35 μg of Streptavidin (manufactured by PIERCE) was added to perform immobilization at 4° C. for 16 hours. After these wells were washed with 90 μl of a washing solution (physiological saline containing 0.01% Tween 20) once, 200 μl of Block Ace (manufactured by Dainippon Sumitomo Pharma Co., Ltd.) was added, and the wells were allowed to stand at room temperature for 2 hours, to perform blocking (a Streptavidin solid-phased plate). After each well was washed with 90 μl of a washing solution once, 15 μl of a buffer A containing each of Biotin-STn(DT*R)-20, Biotin-STn(DT*R)-40, Biotin-STn(DT*R)-60, Biotin-STn(DT*R)-80, and Biotin-STn(DT*R)-100 was added and the reaction was allowed to proceed at room temperature for 30 minutes. Then, after each well was washed with 90 μl of a washing solution three times, 15 μl of a buffer A containing a MUC1 antibody was added and the reaction was allowed to proceed at 4° C. for 16 hours. Then, after each well was washed with 90 μl of a washing solution three times, 15 μl of TMB+Substrate-Chromogen (manufactured by DAKO) was added to develop a color at room temperature for 30 minutes, 15 μl of 0.05 M sulfuric acid was added to stop the reaction, and absorbance at 450 nm was measured. As a result, it was shown that 12D10 has approximately the same reactivity for Biotin-STn(DT*R)-40, Biotin-STn(DT*R)-60, Biotin-STn(DT*R)-80, and Biotin-STn(DT*R)-100 and it is an antibody having low dependency on a length of the tandem repeat (FIG. 2).

(Affinity of Antibody)

Biotin-STn(DT*R)-20 was solid-phased on a Sensor Chip SA (manufactured by GE Healthcare), and a dissociation constant of 12D10 was analyzed using Biacore T100. The result of a dissociation constant $K_D$ of 12D10 was $9.1 \times 10^{-9}$ (M) (Table 3).

TABLE 3

| Clone | ka1 (1/Ms) | Kd1 (1/s) | KD (M) |
|---|---|---|---|
| 12D10 | $2.2 \times 10^4$ | $2.0 \times 10^{-4}$ | $9.1 \times 10^{-9}$ |

(Assessment of Binding of Antibody to Cancer Cell with FACS)

Whether the MUC1 protein expressed on a surface of a cancer cell and the 12D10 antibody would bind with each other was examined by FACS (fluorescence activated cell sorting). A human lung cancer culture cell, Calu-3 (ATCC Number HTB-55) and a human breast cancer culture cell strain T-47D (ATCC number HTB-133), cultured with DMEM containing 10% FBS (manufactured by Invitrogen) as well as a human mammary gland cell 184A1 (ATCC Number CRL-8798) cultured with Mammary Epithelial Growth Medium (manufactured by LONZA) were collected by Trypsin-EDTA, and then were suspended in PBS (FACS buffer) containing 0.05% sodium azide and 5% FBS. MUC1 antibody was added to reach 5 μg/ml, and the reaction was allowed to proceed at room temperature for 2 hours. The resultant reaction product was washed with a FACS buffer two times, and then FITC label anti-mouse IgG (manufactured by Invitrogen) diluted 200-fold with a FACS buffer was added for a reaction at a room temperature for 1 hour. After washing with a FACS buffer two times, analysis was performed by FACS Aria (manufactured by Bection, Dickinson and Company). As a result, in T-47D, the 12510 antibody shifted the fluorescent signal 140-fold, while in Calu-3, the 12D10 antibody shifted the fluorescent signal 40-fold, as compared with a control mouse IgG2a antibody (manufactured by SIGMA-ALDRICH). However, in 184A1, the fluorescent signal was shifted 2-fold. That is, there were 20 to 70-fold differences. From this result, it was indicated that the 12D10 antibody strongly reacts with MUC1 expression cells having a cancer-associated structure, such as breast cancer cells and lung cancer cells, while the 12D10 antibody hardly reacts with MUC1 expression cells having a normal tissue-associated structure, such as a mammary gland epithelial cell (FIG. 3).

Example 4

Quantification of MUC1 Using 12D10 Antibody

Sandwich immunoassay for quantitating MUC1 was performed according to the following method. 100 μl of a phosphate buffer (50 mM sodium phosphate, 150 mM NaCl, pH 7.4) containing 1 μg of Streptavidin (manufactured by Pierce) was added to a 96-well microtiter plate (manufactured by Nunc) and the fixation reaction was carried out at 4° C. for 16 hours. After these wells were washed with 250 μl of a washing solution (physiological saline containing 0.01% Tween 20) once, 300 μl of Block Ace (manufactured by Dainippon Sumitomo Pharma Co., Ltd.) was added, and this mixture was allowed to stand at room temperature for 2 hours for blocking. After each well was washed with 250 μl of a washing solution two times, 100 μl of a buffer A (50 mM Tris buffer containing 0.9% NaCl, 0.5% BSA, 0.01% Tween 80, and 0.5% ProClin, pH 7.5) containing 100 ng of a biotinated 12D10 antibody was added and the reaction was allowed to proceed at room temperature for 1 hour. After each well was washed with 250 μl of a washing solution two times, 100 μl of a standard solution (T-47D culture supernatant) was added, and this mixture was allowed to stand at 4° C. for 16 hours. After each well was washed with 250 μl of a washing solution three times, 100 μl of a buffer A containing 50 ng of a HRP-labeled 12D10 antibody was added and the reaction was allowed to proceed for 1 hour. After each well was washed with 250 μl of a washing solution three times, 100 μl of TMB+Substrate-Chromogen (manufactured by DAKO) was added to develop a color at room temperature for 30 minutes, 100 μl of 0.05 M sulfuric acid was added to stop the reaction, and absorbance at 450 nm was measured. From this result, it is possible to quantitate MUC1 by sandwich immunoassay using the 12D10 antibody. In addition, the unit (U/ml) of a standard solution (T-47D) was determined from a value upon measurement of a standard antigen attached to a sialated sugar chain antigen KL-6 kit (A test KL-6, Sanko Junyaku Co., Ltd.), in a sandwich immunoassay with the 12D10 antibody. FIG. 5 shows a standard curve.

As described above, the present invention is exemplified by the use of its preferred embodiments of the present invention. However, the present invention should not be interpreted solely based on the embodiments described above. It is understood that the scope of the present invention should be interpreted solely based on the claims. It is also understood that a person skilled in the art can implement equivalent scope of technology, based on the description of the present invention and common knowledge from the description of the detailed preferred embodiments of the present invention. Furthermore, it is understood that any patent, any patent application and any references cited in the present specification should be incorporated by reference in the present specification in the same manner as the contents are specifically described therein.

INDUSTRIAL APPLICABILITY

An antibody capable of recognizing the difference between normal cells and cancer cells at a sugar chain structure level has been provided. The antibody having such a feature is useful as a medicament, a diagnostic drug as well as a research reagent.

SEQUENCE LISTING FREE TEXT

SEQ ID NO.:1: Amino acid sequence of Tn20-mer
SEQ ID NO.:2: Amino acid sequence of heavy chain variable region, of antibody 12D10
SEQ ID NO.:3: Amino acid sequence of light chain variable region of antibody 12D10
SEQ ID NO.:4: Amino acid sequence of CDR1 of antibody 12D10
SEQ ID NO.:5: Amino acid sequence of CDR2 of antibody 12D10
SEQ ID NO.:6: Amino acid sequence of CDR3 of antibody 12D10
SEQ ID NO.:7: Amino acid sequence of CDR1' of antibody 12D10
SEQ ID NO.:8: Amino acid sequence of CDR2' of antibody 12D10 SEQ ID NO.:9: Amino acid sequence of CDR3' of antibody 12D10
SEQ ID NO.:10: Minimum sequence recognition APDTR-PAP
SEQ ID NO.: 11: Sequence SAPDTRP in the MUC1 tandem-type repeat
SEQ ID NO.:12: Pentamer PDTRP

The invention claimed is:

1. A purified antibody or an antigen-binding fragment thereof, comprising at least one antigen-binding site including an immunoglobulin heavy chain variable region (VH) domain and an immunoglobulin light chain variable region (VL) domain,
the heavy chain variable region domain containing hypervariable regions, CDR1, CDR2 and CDR3, in a sequence thereof, wherein the CDR1 consists of SHDMS (SEQ ID NO: 4), the CDR2 consists of AINSDGDNTYYPDTMER (SEQ ID NO: 5), and the CDR3 consists of LTLRNWYFDV (SEQ ID NO: 6),
the light chain variable region domain containing hypervariable regions, CDR1', CDR2' and CDR3', in a sequence thereof, wherein the CDR1' consists of KSSQSLLYSTNQQNYLA (SEQ ID NO: 7), the CDR2' consists of WASTRES (SEQ ID NO: 8), and the CDR3' consists of QQYYRYPPT (SEQ ID NO: 9).

2. The antibody or the antigen-binding fragment thereof according to claim 1, further comprising SEQ ID NOs: 2 and 3.

3. A medical composition comprising the antibody or the antigen-binding fragment thereof according to claim 1.

4. The medical composition according to claim 3, which is an anticancer agent.

5. A diagnosis kit comprising the antibody or the antigen-binding fragment thereof according to claim 1.

6. An isolated nucleic acid molecule encoding the antibody or the antigen-binding fragment thereof according to claim 1.

7. A method for detecting cancer in a patient, comprising the steps of:
measuring the amount of a cancer-associated structure of MUC1 in a biological sample from the patient using the antibody or the antigen-binding fragment thereof according to claim 1; and
determining that the patient has cancer if the amount of the cancer-associated structure of MUC1 in the biological sample is more than the amount of a cancer-associated structure of MUC1 in a biological sample from a healthy individual without cancer.

8. A medical composition comprising the antibody or the antigen-binding fragment thereof according to claim 2.

9. The medical composition according to claim 8, which is an anticancer agent.

10. A diagnosis kit comprising the antibody or the antigen-binding fragment thereof according to claim 2.

11. An isolated nucleic acid molecule encoding the antibody or the antigen-binding fragment thereof according to claim 2.

12. A method for detecting cancer in a patient, comprising the steps of:
measuring the amount of a cancer-associated structure of MUC1 in a biological sample from the patient using the antibody or the antigen-binding fragment thereof according to claim 2; and
determining that the patient has cancer if the amount of the cancer-associated structure of MUC1 in the biological sample is more than the amount of a cancer-associated structure of MUC1 in a biological sample from a healthy individual.

* * * * *

```
                          SEQUENCE LISTING

<160> NUMBER OF SEQ ID NOS: 12

<210> SEQ ID NO 1
    <211> LENGTH: 20
    <212> TYPE: PRT
    <213> ORGANISM: Artificial
    <220> FEATURE:
    <223> OTHER INFORMATION: Synthetic Construct; Tn20mer

<400> SEQUENCE: 1

His Gly Val Thr Ser Ala Pro Asp Thr Arg Pro Ala Pro Gly Ser Thr
    1               5                   10                  15

Ala Pro Pro Ala
                20

<210> SEQ ID NO 2
    <211> LENGTH: 119
    <212> TYPE: PRT
    <213> ORGANISM: Artificial
    <220> FEATURE:
    <223> OTHER INFORMATION: Synthetic Construct; Antibody 12D10 heavy chain

<400> SEQUENCE: 2

Glu Val Gln Leu Val Glu Ser Gly Gly Gly Leu Val Gln Pro Gly Glu
    1               5                   10                  15

Ser Leu Lys Leu Ser Cys Glu Ser Asn Glu Tyr Glu Phe Pro Ser His
                    20                  25                  30

Asp Met Ser Trp Val Arg Lys Thr Pro Glu Lys Arg Leu Glu Leu Val
                35                  40                  45
```

```
Ala Ala Ile Asn Ser Asp Gly Asp Asn Thr Tyr Tyr Pro Asp Thr Met
        50                  55                  60

Glu Arg Arg Phe Ile Ile Ser Arg Asp Asn Ser Lys Lys Thr Leu Tyr
 65                  70                  75                  80

Leu Gln Met Ser Ser Leu Asn Ser Ala Asp Thr Ala Leu Tyr Tyr Cys
                 85                  90                  95

Ala Arg Leu Thr Leu Arg Asn Trp Tyr Phe Asp Val Trp Gly Ala Gly
            100                 105                 110

Thr Thr Val Thr Val Ser Ser
            115

<210> SEQ ID NO 3
<211> LENGTH: 115
<212> TYPE: PRT
<213> ORGANISM: Artificial
<220> FEATURE:
<223> OTHER INFORMATION: Synthetic Construct; Antibody 12D10 light chain

<400> SEQUENCE: 3

Asp Ile Val Met Ser Gln Ser Pro Ser Ser Leu Pro Val Ser Val Gly
 1               5                  10                  15

Glu Lys Val Thr Met Ser Cys Lys Ser Ser Gln Ser Leu Leu Tyr Ser
                 20                  25                  30

Thr Asn Gln Gln Asn Tyr Leu Ala Trp Tyr Gln Gln Lys Ser Gly Gln
             35                  40                  45

Ser Pro Lys Leu Leu Val Tyr Trp Ala Ser Thr Arg Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Leu Lys Ala Glu Asp Leu Ala Val Tyr Tyr Cys Gln Gln
                 85                  90                  95

Tyr Tyr Arg Tyr Pro Pro Thr Phe Gly Ala Gly Thr Lys Leu Glu Leu
            100                 105                 110

Asn Arg Ala
        115

<210> SEQ ID NO 4
<211> LENGTH: 5
<212> TYPE: PRT
<213> ORGANISM: Artificial
<220> FEATURE:
<223> OTHER INFORMATION: Synthetic Construct; CDR1 of antibody 12D10
      heavy chain

<400> SEQUENCE: 4

Ser His Asp Met Ser
 1               5

<210> SEQ ID NO 5
<211> LENGTH: 17
<212> TYPE: PRT
<213> ORGANISM: Artificial
<220> FEATURE:
<223> OTHER INFORMATION: Synthetic Construct; CDR2 of antibody 12D10
      heavy chain

<400> SEQUENCE: 5

Ala Ile Asn Ser Asp Gly Asp Asn Thr Tyr Tyr Pro Asp Thr Met Glu
 1               5                  10                  15

Arg
```

```
<210> SEQ ID NO 6
<211> LENGTH: 10
<212> TYPE: PRT
<213> ORGANISM: Artificial
<220> FEATURE:
<223> OTHER INFORMATION: Synthetic Construct; CDR3 of antibody 12D10
      heavy chain

<400> SEQUENCE: 6

Leu Thr Leu Arg Asn Trp Tyr Phe Asp Val
1               5                   10

<210> SEQ ID NO 7
<211> LENGTH: 17
<212> TYPE: PRT
<213> ORGANISM: Artificial
<220> FEATURE:
<223> OTHER INFORMATION: Synthetic Construct; CDR1 of
      antibody 12D10 heavy chain(CDR1')

<400> SEQUENCE: 7

Lys Ser Ser Gln Ser Leu Leu Tyr Ser Thr Asn Gln Gln Asn Tyr Leu
1               5                   10                  15

Ala

<210> SEQ ID NO 8
<211> LENGTH: 7
<212> TYPE: PRT
<213> ORGANISM: Artificial
<220> FEATURE:
<223> OTHER INFORMATION: Synthetic Construct; CDR2 of
      antibody 12D10 heavy chain(CDR2')

<400> SEQUENCE: 8

Trp Ala Ser Thr Arg Glu Ser
1               5

<210> SEQ ID NO 9
<211> LENGTH: 9
<212> TYPE: PRT
<213> ORGANISM: Artificial
<220> FEATURE:
<223> OTHER INFORMATION: Synthetic Construct; CDR3 of
      antibody 12D10 heavy chain(CDR3')

<400> SEQUENCE: 9

Gln Gln Tyr Tyr Arg Tyr Pro Pro Thr
1               5

<210> SEQ ID NO 10
<211> LENGTH: 8
<212> TYPE: PRT
<213> ORGANISM: Artificial
<220> FEATURE:
<223> OTHER INFORMATION: Synthetic Construct; a minimal recognition
      sequence of MUC1 reactive monoclonal antibody

<400> SEQUENCE: 10

Ala Pro Asp Thr Arg Pro Ala Pro
1               5

<210> SEQ ID NO 11
<211> LENGTH: 7
<212> TYPE: PRT
<213> ORGANISM: Artificial
<220> FEATURE:
```

```
<223> OTHER INFORMATION: Synthetic Construct; a sequence within
      MUC1 tandem-type repeat

<400> SEQUENCE: 11

Ser Ala Pro Asp Thr Arg Pro
1               5

<210> SEQ ID NO 12
<211> LENGTH: 5
<212> TYPE: PRT
<213> ORGANISM: Artificial
<220> FEATURE:
<223> OTHER INFORMATION: Synthetic Construct; a pentameric sequence

<400> SEQUENCE: 12

Pro Asp Thr Arg Pro
1               5
```